(12) United States Patent
Questo et al.

(10) Patent No.: US 8,756,997 B2
(45) Date of Patent: Jun. 24, 2014

(54) SONIC RESONATOR SYSTEM WHICH APPLIES A RAREFACTION WAVE TO A COMPOSITE STRUCTURE AT A SPECIFIC LOCATION TO TEST BOND STRENGTH

(71) Applicants: Warren Questo, El Dorado Hills, CA (US); Carl W. Hennige, Folsom, CA (US)

(72) Inventors: Warren Questo, El Dorado Hills, CA (US); Robert W. Cribbs, Placerville, CA (US); Carl W. Hennige, Folsom, CA (US)

(73) Assignee: Sonipulse, Inc., Cameron Park, CA (US)

( * ) Notice: Subject to any disclaimer, the term of this patent is extended or adjusted under 35 U.S.C. 154(b) by 0 days.

(21) Appl. No.: 13/694,266

(22) Filed: Nov. 13, 2012

(65) Prior Publication Data

US 2013/0098138 A1    Apr. 25, 2013

Related U.S. Application Data

(62) Division of application No. 12/800,730, filed on May 21, 2010, now Pat. No. 8,347,723.

(51) Int. Cl.
*G01M 7/02* (2006.01)
*G01N 29/12* (2006.01)

(52) U.S. Cl.
USPC ................................ 73/588; 73/1.82; 73/584

(58) Field of Classification Search
USPC ........... 73/584, 588, 763, 774, 781, 818, 821, 73/865.8, 866.5, 1.82
See application file for complete search history.

(56) References Cited

U.S. PATENT DOCUMENTS

| | | | | |
|---|---|---|---|---|
| 3,890,831 A | | 6/1975 | Cusick et al. ................. 73/88 B |
| 4,614,116 A | | 9/1986 | Huston et al. ................... 73/657 |
| 4,633,119 A | * | 12/1986 | Thompson .................... 310/325 |
| 4,843,884 A | * | 7/1989 | House et al. .................... 73/622 |
| 5,421,206 A | | 6/1995 | Rohwedder ..................... 73/834 |
| 5,460,178 A | * | 10/1995 | Hudon et al. ................. 600/443 |
| 5,578,888 A | | 11/1996 | Safabakhsh .................. 310/328 |
| 5,621,656 A | | 4/1997 | Langley ........................ 364/508 |
| 5,661,241 A | * | 8/1997 | Harth et al. ..................... 73/622 |
| 5,748,566 A | * | 5/1998 | Goodson ....................... 367/158 |
| 5,832,412 A | | 11/1998 | Guez .............................. 702/75 |
| 5,908,441 A | * | 6/1999 | Bare ................................ 607/1 |
| 6,122,223 A | * | 9/2000 | Hossack ........................ 367/11 |
| 6,181,431 B1 | | 1/2001 | Siu ............................... 356/502 |
| 6,222,795 B1 | * | 4/2001 | Hossack et al. .............. 367/138 |
| 6,424,150 B2 | * | 7/2002 | Kwun et al. .................. 324/216 |
| 6,490,047 B2 | | 12/2002 | Siu ............................... 356/502 |
| 6,510,104 B1 | * | 1/2003 | Ikegami ......................... 367/31 |
| 6,727,691 B2 | | 4/2004 | Goldfine et al. .............. 324/240 |

(Continued)

OTHER PUBLICATIONS

Bossi et al., "Validating the Strength of Adhesively Bonded Joints", Apr. 18-21, 2011.

(Continued)

*Primary Examiner* — David A Rogers
(74) *Attorney, Agent, or Firm* — Shirley L. Church, Esq.

(57) ABSTRACT

Disclosed herein is a sonic resonator system for use in testing the adhesive bond strength of composite materials. Also disclosed herein are a method of calibrating the sonic resonator system to work with a particular composite bond joint, and a method of non-destructive testing the "pass-fail" of the bonded composite bond strength, based on a required bond strength.

13 Claims, 10 Drawing Sheets

(56) References Cited

U.S. PATENT DOCUMENTS

| | | | |
|---|---|---|---|
| 6,784,662 B2 | 8/2004 | Schlicker et al. | 324/242 |
| 6,813,951 B2 | 11/2004 | Blouin | 73/643 |
| 6,962,082 B2 * | 11/2005 | Hashimoto et al. | 73/579 |
| 7,019,439 B2 * | 3/2006 | DeCastro et al. | 310/325 |
| 7,117,134 B2 | 10/2006 | Dubois et al. | 703/5 |
| 7,123,725 B2 | 10/2006 | Boesch, Jr. et al. | 381/58 |
| 7,220,966 B2 | 5/2007 | Saito et al. | 250/341.6 |
| 7,250,706 B2 * | 7/2007 | Shiba | 310/325 |
| 7,286,241 B2 | 10/2007 | Drake, Jr. | 356/502 |
| 7,393,323 B2 * | 7/2008 | Vago | 600/437 |
| 7,770,454 B2 | 8/2010 | Sokol et al. | 73/588 |
| 7,886,602 B2 * | 2/2011 | Lopatin et al. | 73/584 |
| 2004/0239317 A1 | 12/2004 | Goldfine et al. | 324/240 |
| 2005/0131289 A1 * | 6/2005 | Aharoni et al. | 600/407 |
| 2011/0101824 A1 * | 5/2011 | Nishigaki | 310/317 |
| 2011/0188251 A1 * | 8/2011 | Kalms et al. | 362/259 |

OTHER PUBLICATIONS

Bossi et al., "Laser Bond Inspection Device for Composites: Has the Holy Grail Been Found?", Jun. 2, 2005.

* cited by examiner

SONIC RESONATOR SYSTEM WHICH APPLIES A RAREFACTION WAVE TO A COMPOSITE STRUCTURE AT A SPECIFIC LOCATION TO TEST BOND STRENGTH

This application is a divisional application of U.S. application Ser. No. 12/800,730, filed May 21, 2010, entitled: "Sonic Resonator System For Testing The Adhesive Bond Strength Of Composite Materials", which is currently pending.

FEDERALLY SPONSORED RESEARCH OR DEVELOPMENT

The research underlying this invention was supported in part with funds from the following Federal contracts FA8650-05-N-5032; FA8650-07-N-5047; FA8650-09-C-5035; and N68335-07-C-0093. The United States Government may have an interest in subject matter from this invention.

BACKGROUND

1. Field

The invention relates to the testing of adhesive bond strength of composite materials. The invention also relates to the use of a sonic method of non-destructive testing of bonded composite structures.

2. Description of the Background Art

This section describes background subject matter related to the disclosed embodiments of the present invention. There is no intention, either express or implied, that the background art discussed in this section legally constitutes prior art.

The use of composite bonded joints to replace fasteners on primary load structures used in aircraft has been shown to have a significant impact on reducing the cost of manufacturing airframes. Composite bonded joints are also commonly used in the automobile and boating industries. Repair of composite structures which are used in such industries is an important need. To determine whether the bond in a bonded structure has failed or been reduced in strength, so that a repair is needed, requires a method of non-destructive testing of the bonded structures. One of the barriers preventing the use of bonded composite structures is the risk that a "kissing bond" (i.e., an adhesion bond that is not broken, but is well below the required design strength). There is a need for a non-destructive method of determining whether a bond within a composite meets the required design strength. Conventional nondestructive evaluation techniques are not capable of identifying a 'kissing bond". Even with respect to newly fabricated bonded composite structures, destructive testing of specimens prepared simultaneously in a side-by-side fabrication with the composite article does not ensure that all of the bonds within a fabricated part meet design requirements.

One method of detecting "kissing bonds" would be to produce a negative ultrasonic pulse of such amplitude that it is capable of exceeding the minimal acceptable yield point of the composite bonds. If the bond is above the minimum required design strength and remains intact, it is considered an acceptable bond.

To cause delamination of bonds which do not meet a typical minimum requirement for an aerospace/airframe industry application, for example, it is estimated that a sound pressure greater than about 20 MegaPascal or 2900 psi would be required. In addition, the sound pressure wave would need to be a negative pressure or rarefaction wave to effectively stress the adhesive bond.

There are currently devices that deliver high power sonic energy in the form of a shock or positive pressure compression wave, which is typically applied to the front surface of the material to be tested. This compression pressure wave must then pass completely through the outer, front composite panel, through the adhesive bond and continue through the inner, rear composite panel, and then reflect from the rear surface of the inner, rear panel, reversing the polarity of the wave, to return back to the adhesive interface as a rarefaction or negative pressure wave. A usable bounce would have to occur from a surface that is perpendicular to the incident wave and be at a lower acoustic impedance to produce the desired rarefaction negative pressure wave at the location of the adhesive bond.

One obvious disadvantage of delivering a compression wave is that the sound must travel much further to bounce off the back surface of the inner, rear panel, resulting in less wave intensity due to the increased propagation distance. A major disadvantage of using the compressive wave is that usable areas for testing load bearing structures is limited to structures where the rear surface is parallel to the front surface, and where the rear interface is air or other low acoustic impedance material. If the front, outer composite panel (nearest to entry of the sound wave) is bonded to an inner structure which is metal (higher acoustic impedance), then the reflected wave is a compression, positive pressure wave and not a usable stress wave for non-destructive testing.

Although there are ways for existing sonic devices to create a rarefaction wave, the coupling of a negative pressure sound wave into the material to be tested becomes a significant problem, since the sonic device must not pull away or lose contact with the surface of the material under test.

BRIEF SUMMARY OF THE INVENTION

Embodiments of the present invention overcome the disadvantages of the previously known sonic devices in that the sonic resonator system of the present invention delivers a very high intensity rarefaction (negative pressure) wave, concentrated at any depth within the structure being tested, resulting in a directly applied rarefaction wave to a bonded joint under test. Due to the direct application of this rarefaction wave, there is no need for a reflective rear interface which is perpendicular to the incident wave. Nor does the interface (composite panel) need to be of low impedance (i.e., it can be metal or another material of a higher acoustic impedance).

In general, the apparatus embodiments comprise a sonic generating system which includes a high-intensity sonic resonator assembly. In addition to the high intensity sonic resonator assembly, which transmits sonic energy into a bonded composite structure to be tested, the sonic generating system further comprises an excitation source which generates a low intensity sonic field, a digital-to-analog (D/A) converter, and a power amplifier. A signal capture/calibration device is used in conjunction with a representative sample of the new bonded composite structure during calibration of the system. A computer which contains software algorithms used for signal reconstruction is used to construct the appropriate digital signals which are applied to a D/A converter which provides the excitation wave forms to the sonic resonator assembly. The sonic resonator assembly delivers a high power, wide bandwidth, rarefaction sonic wave to a specific depth in a composite structure being tested.

In an advantageous embodiment, the sonic resonator system includes a "transparent" sound wave receiving capability integrated into the sonic resonator assembly, to support standard pulse-echo non-destructive sonic testing, thereby eliminating the need for a separate device to detect voids and/or delaminations inside the material being tested. The particular voltage waveform that produces the impulse (or stimulus) for calibration purposes and for subsequent power pulse generation during composite structure testing depends upon the resonator design and calibration procedure.

One embodiment of the invention disclosed herein for testing the adhesive bond strength of materials comprises the following components, which are electrically connected in the following sequence.

a computer containing software algorithms for signal reconstruction and waveform generation;

a digital-to-analog converter which is in communication with the computer which generates said wave form;

a power amplifier;

a sonic resonator assembly which is capable of transmitting sonic energy into a sample of a composite material to be tested for adhesion bonding strength;

a pre-amplifier in communication with a transparent receiving piezoelectric element of the sonic resonator assembly; and, an analog-to-digital converter which is present between the pre-amplifier and the computer.

The sonic resonator assembly frequently comprises the following components:

a driver element comprising a piezoelectric disc that is driven by the power amplifier to provide excitation signals into said main resonator assembly;

a main resonator assembly comprising alternating lamina of discs having different acoustic impedances; and, a transparent receiving piezoelectric element which is used to support pulse echo non-destructive testing.

In an alternative embodiment, the transparent receiving piezoelectric element is not present, and a conventional ultrasonic flaw detection/non-destructive testing (NDT) system is used to determine whether the adhesive bond was affected by exposure to the rarefaction wave.

A coupling cone or other equivalent device is used to couple the sonic resonator assembly to a composite structure to be tested.

The main resonator assembly comprises alternating lamina of discs having different acoustic impedances. Each disc may have a flat surface or may have at least one kerf in the surface, to control radial mode surface waves. Typically, the alternating lamina of discs comprise alternating high acoustic impedance and low acoustic impedance materials. The impedance ratio of a high acoustic impedance disk to a low acoustic impedance disk typically ranges from about 1.3:1 to 3:1. Expansion of the acoustic impedance characteristics and impedance ratios for the alternating lamina of disks (or other shaped layers) may be developed for particular end-use applications, in view of the disclosure provided subsequently herein.

There are three practical groupings of material that can be effectively used to provide the desirable acoustic ratios between 1.3:1 and 3:1 for the high acoustic impedance and low acoustic impedance discs. Group 1: Materials with an acoustic impedance "Z" close to a typical piezoelectric element used as a driver in the sonic generating system have a "Z" of about 36 M Rayals ($kg/m^2s$). Examples of disc materials with such an acoustic impedance include brass, copper, Kovar, silver, and steel, for example and not by way of limitation. Group 2: Materials with an acoustic impedance significantly lower than the group of materials near the piezoelectric element. Examples include aluminum, titanium, tin, and indium. Group 3: Materials with an acoustic impedance significantly higher than the Group 1 acoustic impedance. Examples include nickel, platinum, gold, and molybdenum.

There are three possibilities for mixing materials from the three above-listed groups of materials: A. Alternate Group 1 materials with lower Z grouping materials from Group 2. B. Alternate Group 1 materials with higher Z grouping materials from Group 3. C. Alternate Group 1 materials with both higher and lower Z grouping materials from Group 3 and Group 2, respectively.

In one advantageous embodiment, where a transparent receiver assembly is not present, the highest Z material (a material from the Group 3 materials) is directly adjacent to the piezoelectric transmitting/driving device, and the final disc of the main resonator assembly is formed of the lowest Z material (a material from the Group 2 materials), since the coupling cone is selected to be close in Z to the Z of the composite material which makes up the panel nearest the entering sound wave. It is also possible to use a lower Z material from Group 2 directly adjacent to the piezoelectric transmitting/driving device and still have the final disc of the main resonator assembly formed of material from Group 2, as shown in FIG. 1H. One illustrative example would be the piezoelectric transmitting/driving device followed by followed by molybdenum (the piezoelectric driver assembly), followed by a first main resonator disc of titanium, followed by a copper disc, followed by an aluminum disc, followed by a brass disc, which is followed by an aluminum coupling cone.

The diameter of each disc within the lamina of discs in the main resonator assembly typically has a "taper" (which is described in detail in the "Detailed Description", below), and the entire lamina of discs takes on a tapered shape. When there are 5 tapered disks within the lamina of disks in a main resonator assembly, for example, the amount of taper of each disc is within the range of about 10% to about 15%, and the amount of taper of the entire lamina of discs ranges from about 40% to about 60%. One skilled in the art can determine the amount of taper in instances where a different number of tapered disks are present.

The transparent receiver assembly which advantageously follows the lamina of disks in the main resonator assembly acts as an additional resonator disc during transmit calibration and transmit power cycles, and as a receiver in pulse echo mode. It is 'transparent' during transmission because it passes all signal energy coming from the other lamina of discs, behaving as an additional resonator disc. As a matter of clarification, the transparent resonator assembly has two very important characteristics. One is to have the same wavelength (for the sum of all three elements making up the transparent resonator assembly) as the other resonating disks or lamina. For example, lambda=1. The other characteristic is for the 3 elements of the transparent receiver assembly to continue the acoustic impedance ratio and sequence with the adjacent discs. The transparent receiver assembly does not necessarily have to continue the taper of the main resonator assembly, because the piezoelectric ceramic which makes up one of the elements of the transparent receiver assembly is brittle and has to be machined by grinding to prevent damage. We have shown that the transparent receiver assembly can function well whether it is tapered or untapered. The taper from the main resonator assembly may be further continued in the coupling cone which follows the transparent receiver assembly.

To meet the "transparent" requirement and behave as an additional resonating disc, the transparent receiver assembly must have the proper thickness and the proper impedance ratio. In an exemplary embodiment, the transparent receiver assembly is made up of a series of three discs, where a piezoelectric element is the center disc. Typically, the first element and the third element have a thickness which provides a wavelength (flight time) of ¼ lambda each. The second element, the piezoelectric element, has a wavelength of about ½ lambda. The thickness of the complete transparent receiver assembly is made to match the wavelength (flight time) through each of the other discs in the main resonator assembly. An advantageous material for the first and third discs of the transparent receiver assembly is a brass alloy which can be very closely matched to the acoustic impedance of the receiver piezoelectric element. For example, the transparent receiver assembly could be placed between two lower impedance or two higher impedance elements to maintain the proper acoustic impedance ratio. In one advantageous embodiment, the transparent receiver assembly is located just before the coupling cone, which may be aluminum or a lower impedance, meeting the proper impedance ratio requirements. As previously discussed, the taper of the main resonator assembly may or may not continue through the transparent receiver assembly. An advantageous diameter of the transparent receiver assembly is about 1 inch (2.54 cm) or 50% to 75% of the diameter of the driver piezoelectric element.

A coupling cone may be used to couple the sonic resonator assembly to a composite joint to be adhesion bond tested. The coupling cone is specifically designed to continue the alternating lamina scheme, being of the correct ratio of impedance corresponding to the previous transparent receiver assembly. The material making up the coupling cone may be of the lower impedance metallic material which is used in the main resonator stack of alternating lamina material, to better match the acoustic impedance of the bonded composite material. For example, when the low acoustic impedance material discs comprise aluminum, the coupling cone typically is also formed from aluminum. The coupling cone continues the taper of the main resonator assembly.

A method of calibrating a sonic resonator assembly for use during testing of a bonded composite structure is provided herein. The method comprises the following:

providing a sonic resonator assembly;

positioning a sample of composite material between said sonic resonator assembly and an acoustic capture device, wherein said sample of composite material is about equal in thickness and composition to a composite panel through which a sonic wave from said sonic resonator assembly will first pass during testing of the bonded composite structure;

constructing a broadband impulse which is capable of exciting or stimulating the sonic resonator assembly;

applying the broadband impulse to the sonic resonator through a power amplifier;

measuring a calibration response to the impulse signal using the acoustic capture device after passing the impulse through the sample of composite material;

processing the calibration response collected by the acoustic capture device using an amplitude function algorithm to construct a power packet to be applied to the resonator assembly; and, applying the power packet to the resonator assembly to produce a high power wide bandwidth rarefaction pulse which may be concentrated at a desired interface within a bonded composite structure.

Typically, the thickness and composition of the sample of composite material is the same as the thickness and composition of the first panel of a bonded composite structure through which the rarefaction pulse is to pass during testing of the bonded composite structure.

It is important that the shape, polarity, and bandwidth of the signal used to stimulate the resonator for calibration be performed in accordance with the calibration procedure Step 1 described in the Detailed Description, below. The signal captured is collected over a selected period of time, or a window of time. The signal window start time would normally be upon arrival of the first wave from stimulation. Due to the sound propagation delay from the stimulus (impulse) to arrival at the capture device, a delay is used to "gate" or hold off the start of data collection, to determine the window start time. The data window ends when the signal-to-noise ratio becomes too small. The window length is typically within the range of about 500 to about 900 microseconds in total time. Additionally, the window length in time is adjusted to be multiples of the surface wave flight time. For example, if the radial Ft is 55 microseconds, a good multiple (×10) for the window size would be 550 microseconds.

After obtaining the calibration information which relates to a bonded composite structure to be tested, the sonic resonator assembly, absent the acoustic capture device, is used to test a bonded composite structure to determine whether the bond meets minimal requirements. The method of using the sonic resonator assembly to test a bonded composite structure includes the following steps:

providing a sonic resonator assembly;

coupling the sonic resonator assembly to a bonded composite structure including an adhesion bond to be tested; and applying a controlled broadband signal to the sonic resonator system, based on a calibration response previously measured for a composite material which is part of the composite structure, so that a high power controlled bandwidth rarefaction pulse is concentrated at a location of the adhesion bond in the bonded composite structure.

When the sonic resonator assembly includes a "transparent" receiver assembly, a non-destructive pulse echo sequence is applied to generate a pass/fail indication at the location of the adhesion bond. The pass/fail indication relates to the degree (if any) of delamination between the bonding adhesive and the composite panels bonded by the bonding adhesive. It is also possible to examine the condition of the degree of delamination subsequent to exposure of the bonded composite to the rarefaction pulse using other kinds of imaging apparatus, such as an ultrasonic flaw detector.

BRIEF DESCRIPTION OF THE DRAWINGS

With reference to FIG. 1A, this power packet is generated in computer 110 and passed through the D/A converter 120 and power amplifier 130 to the resonator assembly 140 which will produce a high power, wide bandwidth rarefaction pulse concentrated (focused) at the location where the acoustic capture device 190 was present during calibration of the sonic resonator system 100.

FIG. 8A show a surface view and matching cross-sectional view of a resonator disc 802 which has a radial kerf 808 cut into a surface 803 of disc 802. The purpose of the radial kerf is to align in time the radial surface wave with the plane wave reverberation in a given disk, to improve the efficiency of the resonator assembly. A number of kerfs may be used on a disc surface, depending on the diameter of the disc.

FIG. 8B shows a cross-sectional view of FIG. 8A, illustrating the radial kerf 808 and the depth and width of the kerf.

DETAILED DESCRIPTION OF EXEMPLARY EMBODIMENTS

Figure 1A:
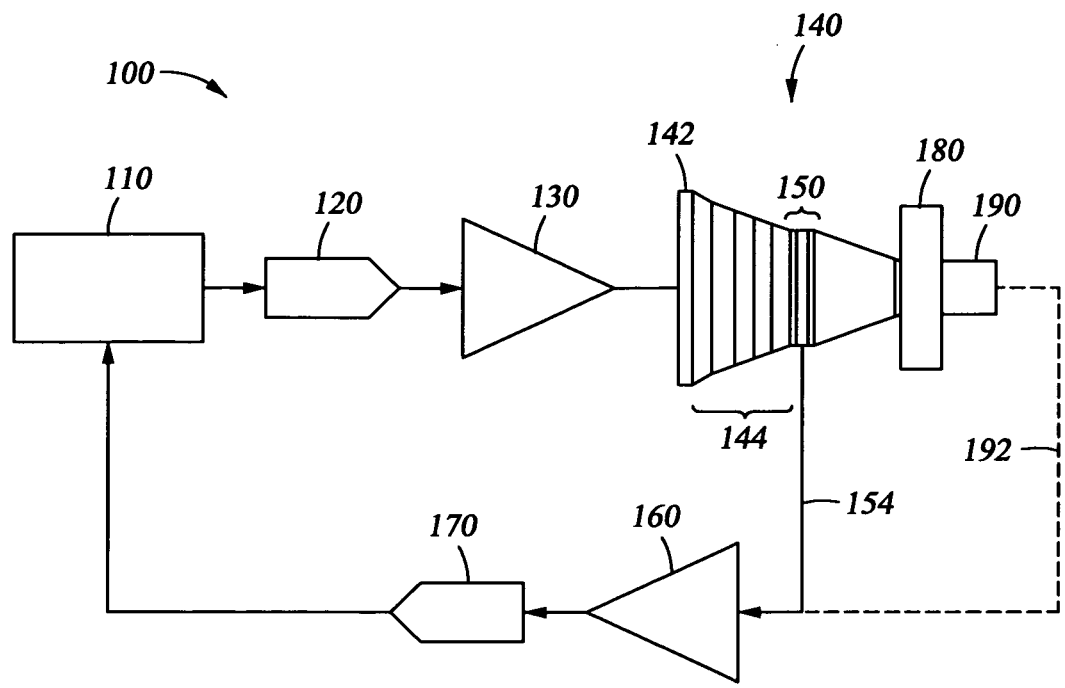
FIG. 1A is a schematic diagram of a typical embodiment of the sonic resonator system 100 of the invention.

As a preface to the detailed description, it should be noted that, as used in this specification and the appended claims, the singular forms "a", "an", and "the" include plural referents, unless the context clearly dictates otherwise.

When the word "about" is used herein, this is intended to mean that the nominal value presented is precise within ±10%.

1. Mathematical Analysis

It is well-known that most systems can be understood and analyzed in either the frequency or time domain. Both domains will be used in describing the present invention. Either method could be used, but the use of both provides nuances that illustrate various aspects of the invention. The following mathematical analysis establishes the design requirements for the sonic resonator assembly and the calibration procedure:

Consider a voltage signal V(t) for the time t between 0 and T. This can be represented by a discrete series of n voltages $V_i$, where:

$$V_i \geq V(i\Delta t)\ i=0,1,\ldots,n$$

and $$n = T/\Delta t$$

A. Frequency Domain Analysis

The discrete Fourier sine transform of this signal is:

$$a_i = \sum_j V_j \sin(2\pi ij/n)$$

And the cosine transform is:

$$b_i = \sum_j V_j \cos(2\pi ij/n)$$

And the amplitude transform is:

$$A_i = \sqrt{a_i^2 b_i^2}$$

And the phase transform is:

$$\theta_i = \tan^{-1}(a_i/b_i)$$

The signal is completely defined by either $a_i$ or $b_i$, or by $A_i$ and $\theta_i$, that is, given either set of numbers, the original signal can be calculated by the inverse Fourier transform. These operations (the Fourier and inverse Fourier transforms) are operations supported by practically all computer languages that are used for mathematical operations, and will not be further defined in this invention. It will be convenient to use the amplitude and phase rather than the sine and cosine representation of the Fourier transforms in the following discussion.

Consider a system (such as the sonic resonator of the present invention) that produces a phase shift of each frequency component of the input signal by some measurable amount $\theta_s(f)$. Suppose that it is desired that the output signal be an impulse at some specific time T and phase $\theta_o$, i.e., a signal with a linear phase transform with a specific slope:

$$\theta_d(f) = kf + \theta_o$$

where:
k=slope=$2\pi T$
$\theta_o$=phase of the desired impulse
T=time when the impulse occurs The phase transform $\theta_a(f)$ of the signal when applied to the resonator that will produce this impulse is:

$$\theta_a(f) = \theta_d(f) - \theta_s(f) + \theta_o$$

In order to take the inverse transform to define the applied signal, an amplitude transform is required. A large variety of wide band functions can be used. Some suitable functions will be discussed below.

B. Time Domain Analysis

The present invention can be understood by analysis in the time domain, i.e., requiring no Fourier transforms. The general approach is to imagine the transducer transmitting an impulse function (a Dirac delta function) into the resonator and finding the response. This can be convolved with the transmitted function to find the actual response.

The Dirac delta function is defined as follows:

$$\delta(t - t_o) = 0 \quad \text{if } t \neq t_o$$
$$= \text{A special kind of infinity if } t = t_o$$

It is special in that:

$$\int_A^B \delta(t - t_o) dt = 1 \quad \text{if } A \leq t_o \leq B$$
$$= 0, \quad \text{otherwise}$$

and $$\int_A^B f(t) \delta(t - t_o) dt = f(t_o) \quad \text{if } A \leq t_o \leq B$$
$$= 0, \quad \text{otherwise.}$$

The theoretical response, R(t) of the resonator to an input impulse function $\delta(t)$ can be written as follows:

$$R(t) = \Sigma_i A_i \delta(t - t_i)$$

where:
$t_i$=the output time of the $i^{th}$ reverberation, and
$A_i$=the amplitude of the reverberation.

The practical consequence of this is that the drive function can be obtained as follows:

1. Drive the transducer-resonator with some impulse function, I(t).
2. Measure the system response, R(t).
3. Time reverse the system response, R(T−t).
4. Normalize R(T−t) by multiplying it by a smooth function. Normally, the amplitude of the response decays by $\epsilon^{-t}/Td$, so multiplying R(T−t) by $\epsilon^{+t}/Td$ results in a function $f(t)$ which is uniform in amplitude from t=0 to T.
5. Drive the resonator with $f(t) = \epsilon^{+t}/Td * R(T-t)$.

The result is an impulse out of the resonator at t=T. This demonstrates how the drive function may be obtained by analyzing the system in the time domain. A high amplitude impulse can be generated by using a drive function which is the time-reversed drive function normalized to the sum of constant amplitude delta functions:

$$D(t) = \Sigma \delta(T - t_i) \text{ sign}(A_i)$$

The sign $A_i$ is provided because $A_i$ may be positive or negative, so the normalized drive function has delta functions that have amplitudes of either +1 or −1.

The system response to this is then:

$$R_A(t) = \Sigma_i \Sigma_j |A_i| \delta(T - t_i + t_j)$$

Note that when i=j, $R_p(t) = \Sigma_i |A_i| \delta(T)$

In other words, the amplitude at T is the sum of all the echoes, whereas at other times of $t_i - t_j$, the amplitude is just $|A_i|$. The actual output is $R_p(t)$ convolved with the actual drive function.

2. Sonic Resonator System

FIG. 1A is a cross-sectional schematic diagram of a typical embodiment of the sonic resonator system 100 of the invention. The system 100 includes a central component, the sonic resonator assembly 140, which transmits sonic energy into a sample of a composite material 180 to be tested for adhesion bonding strength. A computer 110 contains software algorithms that construct the appropriate digital signal that is then applied to the digital-to-analog (D/A) converter 120. A power amplifier 130 couples the D/A converter 120 to a piezoelectric driver element 142 which is part of the sonic resonator assembly 140.

An acoustic capture device 190 is used for purposes of calibration to measure the resonator output after passing through the sample of composite material 180 to be tested. The acoustic capture device 190 is used only during the initial calibration procedure, and needs to be used just once for each type and thickness of composite material. During the calibration procedure, the acoustic capture device 190 is electrically connected to the computer 110 through a pre-amplifier 160 and an analog/digital (A/D) converter 170, as indicated by the dotted line path 192. The data is then stored in the computer 110. The details of the signal capture process (calibration) will be described in detail in Section 3, below, which relates to a "Method of Calibrating the Sonic Resonator System".

A receiving piezoelectric element 146 is used to support pulse echo non-destructive testing. During material testing, the receiving piezoelectric element 146 is electrically connected to the computer 110 through pre-amplifier 160 and A/D converter 170, as indicated by the solid line path 154.

Figure 1B:
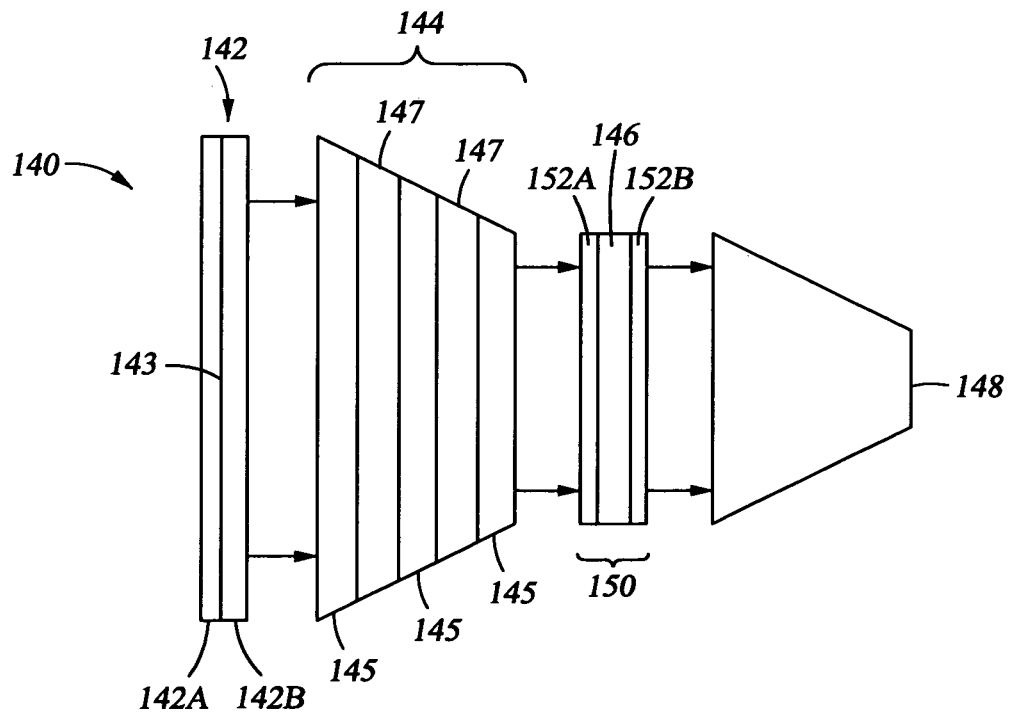
FIG. 1B is an expanded cross-sectional diagram of the sonic resonator assembly 140 shown in FIG. 1A.

FIG. 1B is an expanded cross-sectional side-view schematic of the sonic resonator assembly 140 shown in FIG. 1A. The sonic resonator assembly 140 can be broken down into four sub-assemblies, as follows:

1. A piezoelectric driver element 142 made up of a piezoelectric disc that is driven by a power amplifier 130 (shown in FIG. 1A) to provide excitation signals into a main resonator assembly 144.

2. The main resonator assembly 144 comprising alternating lamina of discs (145, 147) having different acoustic impedances.

3. A transparent receiver assembly 150, including piezoelectric element 146 acts as an additional resonating disc during transmit and as a receiving element at other times.

4. A coupling cone 148 serves as an acoustic interface between the sample of composite material and the sonic resonator assembly.

The piezoelectric driver element 142 comprises a standard commercial piezoelectric element available from various suppliers, such as, for example, Keramos Advanced Piezoelectrics available from Channel Industries, Santa Barbara, Calif., and piezoelectric elements available from Piezo Technologies, Indianapolis, Ind.

With reference to FIG. 1B, the resonate frequency and size (diameter) of the piezoelectric driver element 142 is chosen to be optimal based on the characteristics of the material to be tested. Some typical examples of piezoelectric element materials of interest include Lead Zirconate Titanate (PZT) and Lead Titanate (PT). One of skill in the art of piezoelectric driver elements can select the proper piezoelectric material frequency and size for a given bonded composite application. A piezoelectric driver element 142 can be any diameter, but for many of the embodiments described herein, typically ranges between about 0.5" and about 3" in diameter. The frequency of the piezoelectric driver element 142 and the resonating characteristics (i.e., flight time) of the alternating lamina of discs (145, 147) to which it is attached are also matched.

The main resonator assembly 144 consists of alternating metallic discs (145, 147) having different acoustic impedances (Z). A description of some possible embodiments of the acoustic impedance characteristics and relative impedance ratios for the lamina in the stack of discs which make up the resonator body was previously described herein. Materials with impedances similar to piezodielectrics which are suitable for use in the present invention, include copper, brass and Kovar (a nickel-cobalt ferrous alloy), for example and not by way of illustration. Kovar has an additional desirable characteristic in that its coefficient of expansion is nearly identical to piezoelectric ceramic, which would prevent stress on the adhesive bond and the ceramic with thermal expansion/contraction. Low acoustic impedance materials suitable for use in the present invention include aluminum, tin, titanium, and indium, by way of example and not by way of limitation. High acoustic impedance materials suitable for use in the present invention include nickel, platinum, gold, and molybdenum, by way of example and not by way of limitation.

With reference to previously described acoustic impedance materials, one particularly useful combination of high/low acoustic impedance materials is copper ($Z=43 \times 10^6$ Rayls) and aluminum ($Z=17 \times 10^6$ Rayls) (where 1 Rayl=1 kg/m$^2$·sec; see, for example, J. Krautkrämer et. al., *Ultrasonic Testing of Materials*, Springer Publishing Company, New York, 1990). For example, a typical lamina of discs might have between five and seven alternating high Z discs 145 and low Z discs 147. The alternating lamina of discs (145, 147), along with the receiving piezoelectric element 146 and the coupling cone 148, provide a total of seven to nine resonating elements.

It is advantageous to refer to the plate thickness of the discs in the resonator stack in terms of the wavelength (lambda) of the piezoelectric element 142A which is present in the piezoelectric driver element 142. For example, the piezoelectric element's "effective thickness" is ½ lambda (or its one way flight time) times the velocity of sound in the piezoelectric material. Referencing to lambda allows for scaling of the lamina of disc thicknesses as a function of the resonant frequency of the piezoelectric element and allows for the thickness of each disk per its characteristic sound velocity. Typically, each of the discs in the laminate, other than the disc which is in closest proximity to the driver piezoelectric element, has the same effective thickness, which is equal to 1 lambda. A typical construction would have the piezoelectric element 142A as ½ lambda, the directly adjacent disc 142B having an effective thickness equal to ¾ lambda, and the remaining discs having an effective thickness of 1 lambda each. The piezoelectric element may be selected from materials such as lead zirconate titanate (PZT) and lead titanate (PT), for example and not by way of limitation.

The amplitude coefficients of the reflected R and transmitted T acoustic waves at each interface of the lamina are:

$$R = \frac{Z_1 - Z_2}{Z_1 + Z_2}$$

$$T = \frac{2Z}{Z_1 + Z_2}$$

Where: $Z_1$=Impedance of material containing the wave before the interface; and $Z_2$=Impedance of material containing the wave after the interface.

The reflection coefficient may be negative, in which case a negative impulse is reflected. If the difference in impedance between the lamina were near zero, there would be no acoustic reverberation, that is, the input signal would travel to the output with little energy retention. On the other hand, if there is too large a difference in impedance between the lamina, the signal would reverberate so many times that it would attenuate (i.e., turn into heat) before emerging.

Impedance ratios within the range of 1.3:1 to 3:1 and, more typically, within the range of 1.5:1 to 2.5:1, are acceptable. Examples of metals which have desirable characteristics for machining and which can be used in combination to provide impedance ratios within a range of about 1.5:1 to 2.5:1 between pairings are, for example, copper:aluminum; brass: tin; Kovar:aluminum; and molybdenum:titanium. If the attenuation coefficient of the material is low (like titanium), higher reflection coefficients can be used because the wave can reflect a greater number of times without excess attenuation. Kovar® has an additional desirable characteristic in that it's coefficient of expansion is nearly identical to piezoelectric ceramic, which prevents stress on an adhesion bond and the ceramic due to thermal expansion/contraction.

It might seem that having multiple discs of the same thickness would produce a strong resonance. There is only one path from the receiving piezoelectric element 146 to the output through coupling cone 148; however, that signal is weak because of all of the reflections from the number of reflective interfaces along the way from the piezoelectric driver element 142 to the piezo electric element 146. In the entire resonator assembly 140, which comprises seven resonating elements, there are 45 paths with two reflections; 1695 paths with four reflections; and over 10,000 paths with six or more reflections, from the piezoelectric driver element 142 to the output from receiving piezoelectric element 146.

This multitude of reflections results in "resonances" at a wide range of frequencies; in other words, a broad band resonator. The adhesive bonds between the lamina must be strong to withstand the high stresses produced by the resonating build-up of sonic energy, especially near the output end of the resonator assembly. Low viscosity two-part adhesives typically have sufficient bond strength, but if not, the discs can be bonded using a vacuum diffusion process in a manner that produces bonds as strong as the parent metal.

Figure 1C:
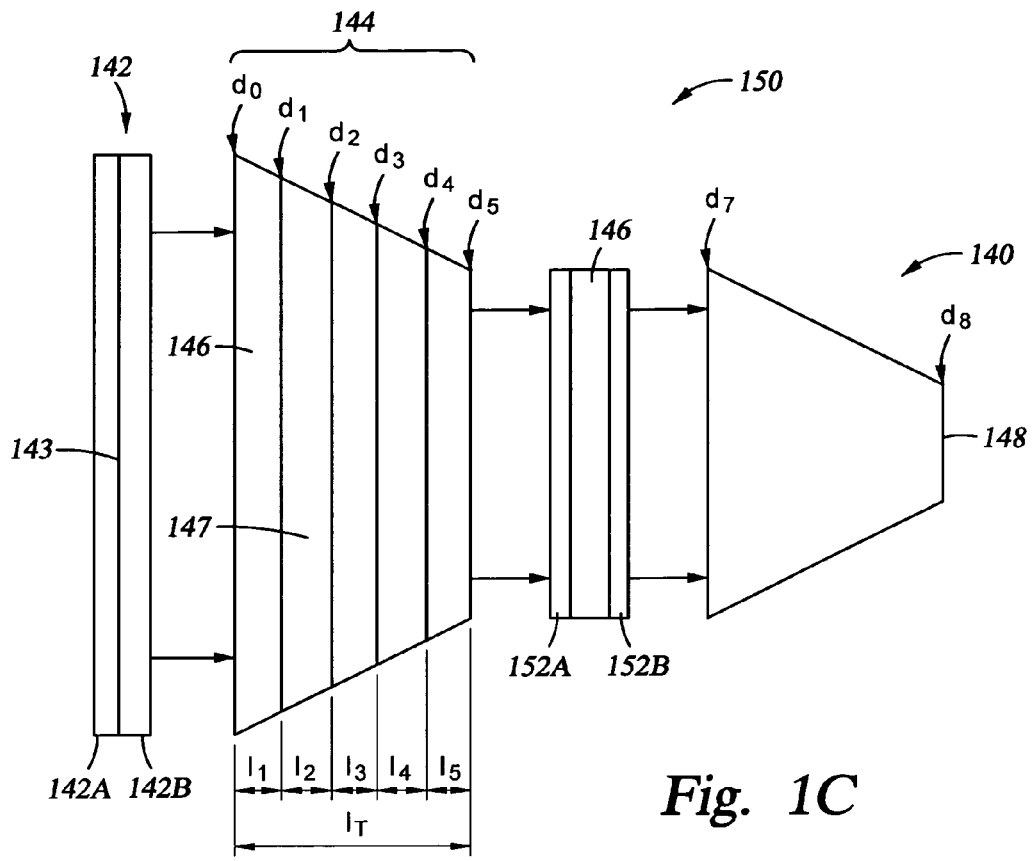
FIG. 1C is an expanded cross-sectional schematic of the sonic resonator assembly 140 shown in FIG. 1B, illustrating the "taper" of the diameter of the discs in the lamina of discs.

As shown in FIG. 1B, which shows the sonic resonator assembly, the diameter of each disc within the lamina of discs which make up main resonator assembly 144 should have a "taper". Each disc progressing from the piezoelectric driver element 142 up to the receiving piezoelectric element 146 should have a larger diameter (d) at the side of the disc ($d_0$), for example, that is closer to the piezoelectric driver element 142, decreasing to a smaller diameter ($d_5$) for example, at the side of the disc that is closer to the receiving piezoelectric element 146. In addition, each disk has a length l. This design requirement is shown in FIG. 1C, which shows an expanded view of the lamina of discs present in main resonator assembly 144. The total length of the taper for main resonator assembly 144 is the sum ($\Sigma$) of lengths $l_1$ through $l_5$. The total amount of the taper is the largest diameter $d_0$ minus the smallest diameter $d_5$. The degree of taper is the length of the taper divided by the amount of the taper, so the degree of taper is equal to $\Sigma\, l_1$ through $l_5 \div (d_0 - d_5)$.

The taper is necessary to reduce the "edge" effects (radial vibration mode and effects of beam spread) and to support the need to have a smaller contact area (at the end of the coupling cone) which must be coupled to the bonded composite which must be tested. These edge effects result in sonic losses along the radius of each of the discs that make up the resonator assembly. First, there is beam spread, in which some of the lateral sonic energy spreads from being a pure plane wave having an oblique bounce off the sides of the sonic device, producing sonic energy losses. In addition, the radial mode vibrations present from the piezoelectric and metallic discs can be destructive to the plane wave. To minimize these edge or loss effects, the diameter of each disc in the lamina of discs is changed to give the resonator assembly a taper. The taper in the sonic resonator assembly 140 shown in FIG. 1C is a linear taper. In the alternative the taper may be an exponential taper (not shown).

When the taper is linear, the percentage of taper (diminishing width divided by length of the element ×100) of each disc is the same and the percentage of taper for the entire lamina of discs is the same. In the exemplary embodiment of the invention described herein, the percentage of taper was about 50%. It is contemplated that the percentage of linear taper of the main resonator assembly may vary from about 20% to about 70%.

Figure 1D:
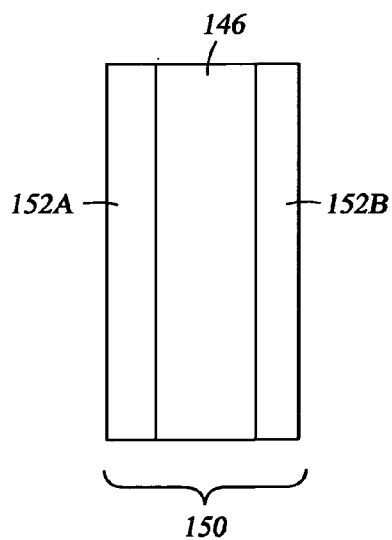
FIG. 1D shows an expanded cross-sectional diagram of the "transparent" receiver assembly 150 shown in FIG. 1B.
Figure 1E:
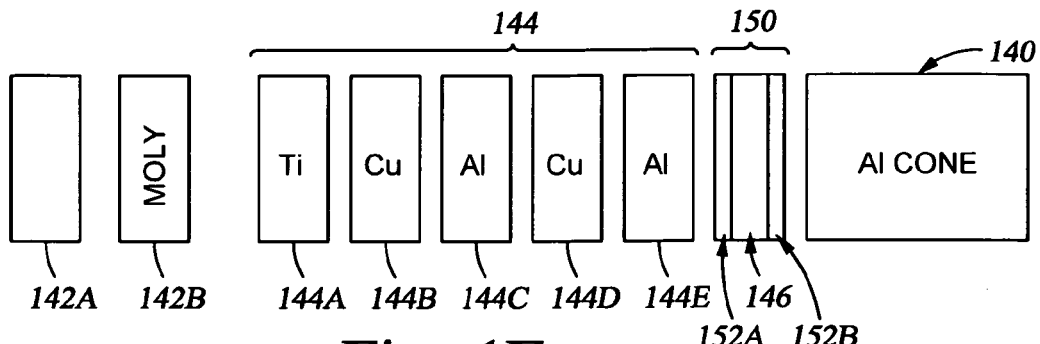
FIG. 1E is a diagram showing an ordering of discs in a resonator assembly which includes a transparent receiver assembly and a coupling cone, where a high Z metal disk is located directly adjacent to the piezoelectric element which makes up a driving piezoelectric assembly.

FIG. 1D shows an expanded cross-sectional schematic of the "transparent" receiver assembly 150 shown in FIG. 1B. The "transparent" receiver assembly 150 acts as an additional resonator disc during transmit calibration and transmitted power cycles, and as a receiver in pulse echo mode. It is "transparent" during transmission because it passes all signal energy coming from the other lamina discs, behaving as an additional resonator disc. To support this requirement to behave as an additional resonating disc, it must have the proper thickness and maintain a 1:1.3 to 1:3 impedance ratio. The transparent receiver assembly 150 (including all three elements), when present, is ratioed with respect to the disk immediately before the assembly, and with the coupling cone 148 immediately following transparent receiver assembly 150.

As shown in FIG. 1D, the transparent receiver assembly 150 comprises the receiving piezoelectric element 146 sandwiched between two discs 152, where the two discs comprise the same material. The material comprising the two discs 152 is selected to match the acoustic impedance of the receiving piezoelectric element 146. Typical piezoelectric materials used in high power applications have an acoustic impedance of 36 MegaRayls (where 1 MegaRayl=1 $kg/m^2 \cdot sec \times 10^6$; see, for example, J. Krautkrämer et. al., *Ultrasonic Testing of Materials*, Springer Publishing Company, New York, 1990). Brass comes in a variety of alloys which span the typical impedance value of the piezoelectric element. One of skill in the art to which the invention belongs will be able to select an appropriate alloy of brass to match the acoustic impedance of the piezoelectric element. The two discs which sandwich the piezoelectric element need to have the closest match to the PZT impedance possible. Therefore the Z of the discs will be near 36 MRayls.

The transparent receiver assembly 150 is constructed to have an effective thickness which is equal in wavelength (lambda) to other discs in the main resonator assembly). For example, if half of the flight time is allocated to the two brass discs and half to the piezoelectric element, the wavelength ($\lambda$) would be allocated to have each brass disc be $0.25\lambda$ in thickness, and the piezoelectric element would be $0.5\lambda$ in thickness.

The required effective thickness of the transparent receiver assembly is calculated using the velocity of sound in the receiving PZT disc multiplied by its allocated flight time, plus the velocity of sound in the metal discs (brass alloy) times its allocated flight time.

In the present exemplary embodiment, the brass discs 152 and the piezoelectric element 146 (collectively, the transparent receiver assembly 150) were of about (within ±10%) the same diameter, which matched the smallest diameter (shown as $d_5$ on FIG. 1C) of the last disc in the lamina of discs (which abuts the transparent receiver assembly 150). While the transparent receiver assembly may continue the taper of the main resonator, due to the brittleness of a typical PZT element, it may be more practical to discontinue the taper after the conclusion of the main resonator assembly 144, so that the transparent receiver assembly has the same diameter as the end diameter $d_5$ of the main resonator assembly.

Referring back to FIG. 1C, the coupling cone 148 is specifically designed to follow the alternating lamina scheme, that is, the coupling cone 148 has an impedance ratio which ranges from 1.5:1 to 2.5:1 relative to the transparent receiver assembly or the disc preceding the cone, if the transparent receiver assembly is not present. This provides a minimum acoustic impedance gradient between the high Z of the transparent receiver assembly and that of the composite, which is typically 4 to 6 MegaRayls.

As shown in FIG. 1C, the coupling cone is tapered. The taper may be either linear or exponential, depending on the taper of the main resonator assembly 144. The coupling cone has an initial diameter which is about the same as the end diameter of the transparent receiving assembly. The coupling cone is tapered to further reduce the resonator assembly's diameter to a smaller tip size. This reduces the contact area so that better contact may be made with the surface to be tested. A contact area having a diameter ranging from about 0.3 inch to about 0.75 inch typically works well.

The largest diameter of the coupling cone 148 (which abuts the transparent receiver assembly 150) should be the same as the diameter of the transparent receiver assembly 150. This diameter is the same as the smallest diameter ($d_5$) of the last disc in the lamina of discs, when the transparent receiving assembly is not tapered, as shown in FIG. 1C. The largest diameter ($d_7$ as shown on FIG. 1C) of the coupling cone 148 is typically within the range of about 1.0 inch to about 2.0 inch. The smallest diameter (shown as $d_8$ on FIG. 1C) of coupling cone 148 is typically within the range of about 0.3 inch to about 0.75 inch, as mentioned above. The taper of the coupling cone may be linear or exponential.

3. Examples of Material Sequences in a Resonator Assembly System:

Examples of typical sequences of material layers making up the main resonator assembly 140 of the kind described with reference to FIG. 1B are illustrated in FIGS. 1E through 1H. The resonator assemblies illustrated include a transparent receiver assembly, while the resonator assemblies illustrated in FIGS. 1F and 1H do not include a transparent receiver assembly.

The piezoelectric driver assembly 142 typically consists of a PZT layer 142A and a layer of high Z metal 142B in direct contact with the surface 143 of PZT layer 142A. The high Z metal layer 142B is facing the main resonator assembly 144. The high Z metal layer is frequently molybdenum. The main resonator assembly 144 includes 5 discs: 144A of titanium, 144B of copper, 144C of aluminum, 144D of copper, and 144E of aluminum. The transparent receiver assembly 150 includes a central layer 146 of a piezoelectric material, which is sandwiched between two layers 152A and 152B of a brass alloy (brass 360, for example). The coupling cone 148 is formed from aluminum.

Figure 1F:
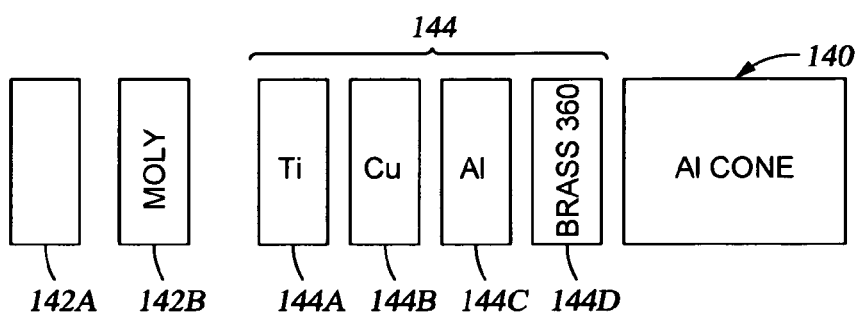
FIG. 1F is a diagram showing an ordering of discs in a resonator assembly which does not include a transparent receiver assembly, where a high Z metal (Group 3 metal) is directly adjacent the piezoelectric element which makes up the driving piezoelectric assembly.

In FIG. 1F, the piezoelectric layer 142A is also in direct contact with a layer 142B of a high Z metal such as molybdenum. The main resonator assembly 144 includes 4 discs: 144A of titanium, 144B of copper, 144C of aluminum, and 144D of brass 360. There is no transparent receiver assembly, and the coupling cone 148 is formed from aluminum.

Figure 1G:
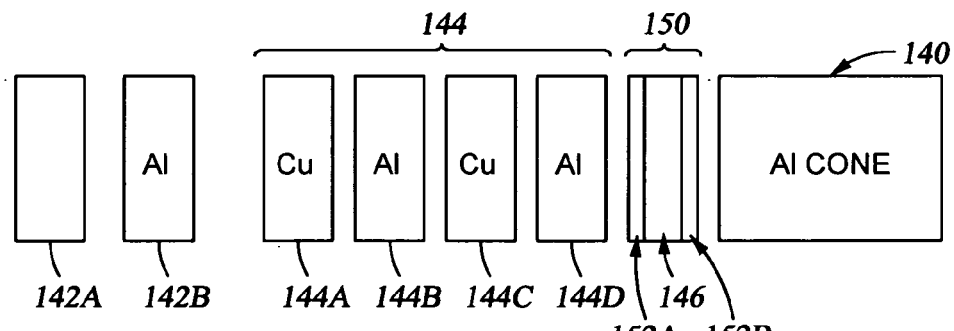
FIG. 1G is a diagram showing an ordering of discs in a resonator assembly which includes a transparent receiver assembly, where a low Z metal (Group 2 metal) is directly adjacent the piezoelectric element which makes up the driving piezoelectric assembly.

In FIG. 1G, the piezoelectric layer 142A is in direct contact with a layer 142B of a low Z metal, aluminum. The main resonator assembly 144 includes 4 discs: 144A of copper, 144B of aluminum, 144C of copper, and 144D of aluminum. The transparent receiver assembly 150 includes a central layer 146 of a piezoelectric material which is sandwiched between two layers 152A and 152B of a brass alloy.

Figure 1H:
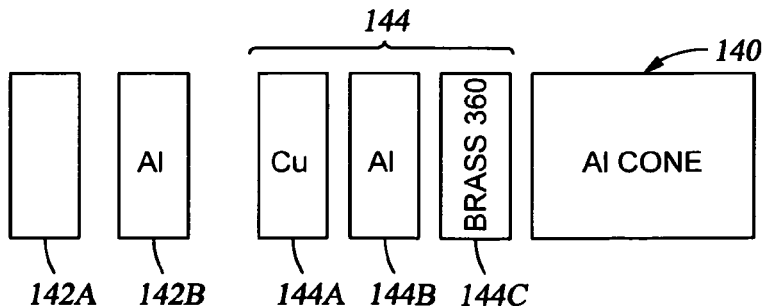
FIG. 1H is a diagram showing an ordering of discs in a resonator assembly which does not include a transparent receiver assembly, where a low Z metal (Group 2 metal) is directly adjacent the piezoelectric element which makes up the driving piezoelectric assembly.

In FIG. 1H, the piezoelectric layer 142A is in direct contact with a layer 142B of a low Z metal, aluminum. The main resonator assembly includes 3 discs: 144A of copper, 144B of aluminum, and 144C of Brass 360. There is no transparent receiver assembly, and the coupling cone 148 is formed from aluminum.

These examples of sequences of material layers are intended to illustrate various possibilities which relate to the design of the main resonator assembly. One skilled in the art will be able to envision other sequences of material layers which may be used within the present invention.

Figure 2A:
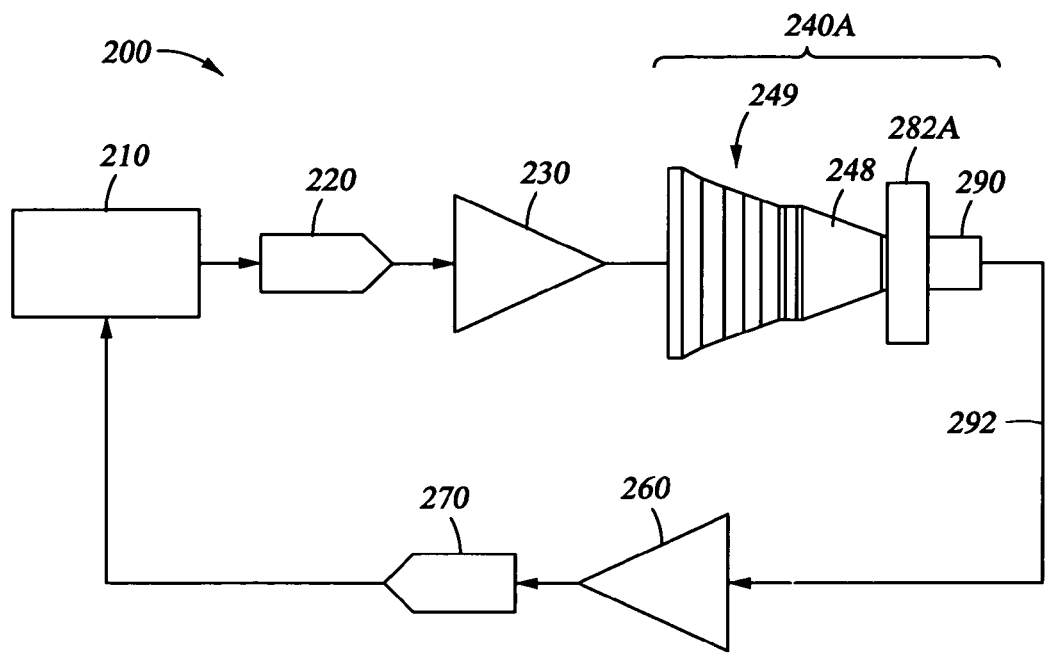
FIG. 2A is a cross-sectional schematic diagram of the elements used in a sonic resonator system 200 during calibration of the system for use during testing of a particular bonded composite structure (not shown). A sample of composite material 282A is illustrated between the sonic resonator assembly 249 and an acoustic capture device 290 which are elements included in an assembly 240A which is used during the calibration process.

4. Method of Calibrating the Sonic Resonator System to Produce a Direct Sonic Rarefaction within the Material to be Tested For the method of the invention to work properly, it is important that the Sonic Resonator System be calibrated to work in combination with the material to be tested. With reference to FIG. 2A, the calibration method comprises the capture of a "calibration" sonic wave being emitted from the sonic resonator assembly 249 by positioning a calibration sensor 290 positioned along the axis of the resonator coupling cone 248, with a sample of the composite structure's outer panel 282A facing the coupling cone. The captured calibration wave form produced is then digitized and passed to the computer 210, where the calibration algorithm described below is used to create a power pulse packet of waveforms to then achieve a "focus" of high sonic intensity at the location where the calibration sensor 290 was previously positioned. For the construction of a rarefaction pulse at a desired location within a material being tested 280 (in FIG. 2B), the power pulse packet of waveforms from the calibration capture are sent to the sonic resonator assembly to reconstruct the rarefaction pulse at a location relative to the material being tested. Once the calibration/capture is complete, multiple rarefaction pulses can be delivered without recalibration as long as the front panel material characteristics and the thickness of the front panel remain the same as those used for calibration.

FIG. 2A is a cross-sectional schematic diagram showing a sonic resonator system 200 in calibration configuration. The system 200 comprises the following major components: computer 210 which acts, at least in part, as a wave generator; digital-to-analog (D/A) converter 220; power amplifier 230; sonic resonator assembly 249; pre-amplifier 260; and analog-to-digital (A/D) converter 270. The system 200 shows a calibration configuration, with a sample of composite material 282A to be used for calibration purposes, and an acoustic capture device 290 in place directly behind the sample 282A, at a location where adhesive bonding material will be present during testing of an actual bonded composite structure.

Figure 2B:
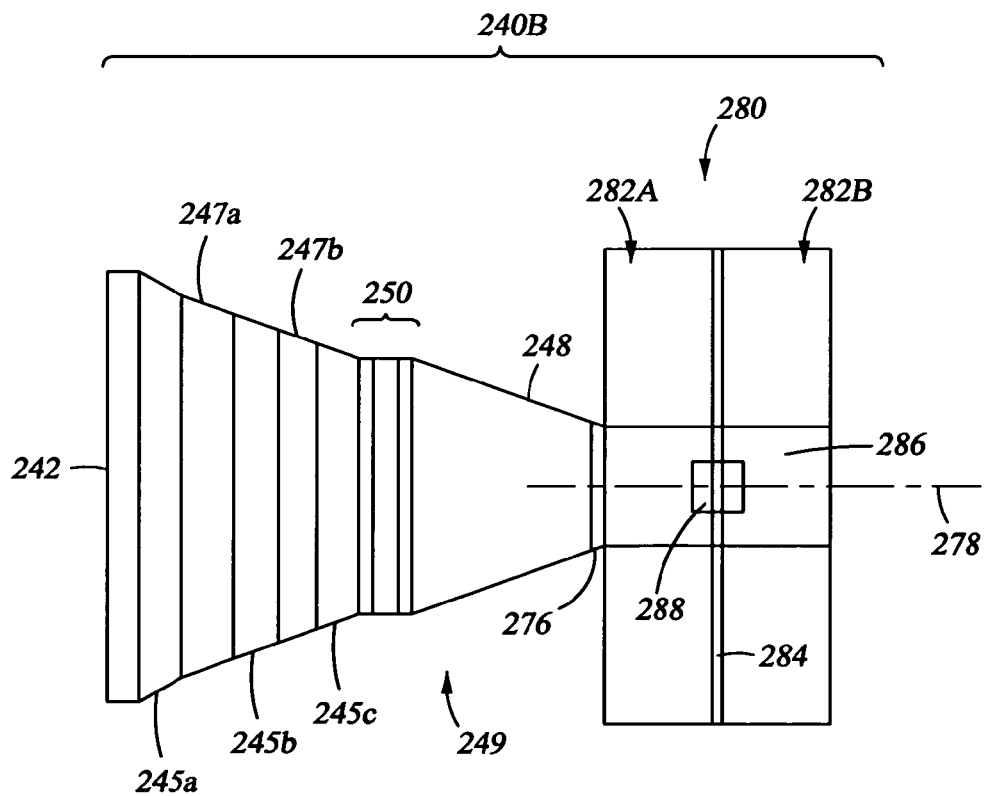
FIG. 2B shows an assembly 240B which is used during a bonded composite structure 280 testing procedure. The sample of composite material 282A and the acoustic capture device 290 used during calibration (as illustrated in FIG. 2A) have been removed, and replaced by the composite structure to be tested 280. The sonic resonator system 200 would be as shown in FIG. 2A, where assembly 240A has been replaced by assembly 240B which is shown in FIG. 2B.

FIG. 2B is an expanded cross-sectional schematic of a combination of the sonic resonator assembly 249 in contact with a bonded composite structure 280 which is to be tested. The sonic resonator assembly 249 comprises piezoelectric driver assembly 242; a lamina of discs (245a, 247a, . . . ), where 245 series discs and 247 series discs have different acoustic impedances from each other; a transparent receiver assembly 250; and a coupling cone 248. (Each of the components which make up the resonator assembly 249 is discussed in more detail in Section 3, above, with reference to the sonic resonator system 100 shown schematically in FIGS. 1A and 1B.)

As shown in FIG. 2B, a sample of a bonded composite structure 280 which is to be tested for adhesion bonding is attached to coupling cone 248. The composite material sample 280 comprises two panels of composite material, 282A and 282B, bonded together by an adhesive material 284.

As a result of the calibration procedure, a high concentration of sonic energy of a desired shape and amplitude after the wave travels into the sample of composite material 282A is produced at the desired depth. The desired depth is indicated as 288 in FIG. 2B. After the calibration process using the assembly 240A illustrated in FIG. 2A, which includes the main resonator assembly 249, coupling cone 248, sample composite material 282A and acoustic capture device 290, it is then possible to achieve a concentration or "focus" of a high sonic intensity rarefaction pulse at a location including adhesive 284 when testing a bonded composites structure of the kind illustrated as 280 in FIG. 2B. The assembly 240A illustrated in FIG. 2A is simply replaced with the assembly 240B which is illustrated in FIG. 2B. A high intensity rarefaction pulse is produced at a location 288 which includes adhesive 284 and composite material along the axis 278 (which is the same axis at which the calibration was carried out.

Figure 4A:
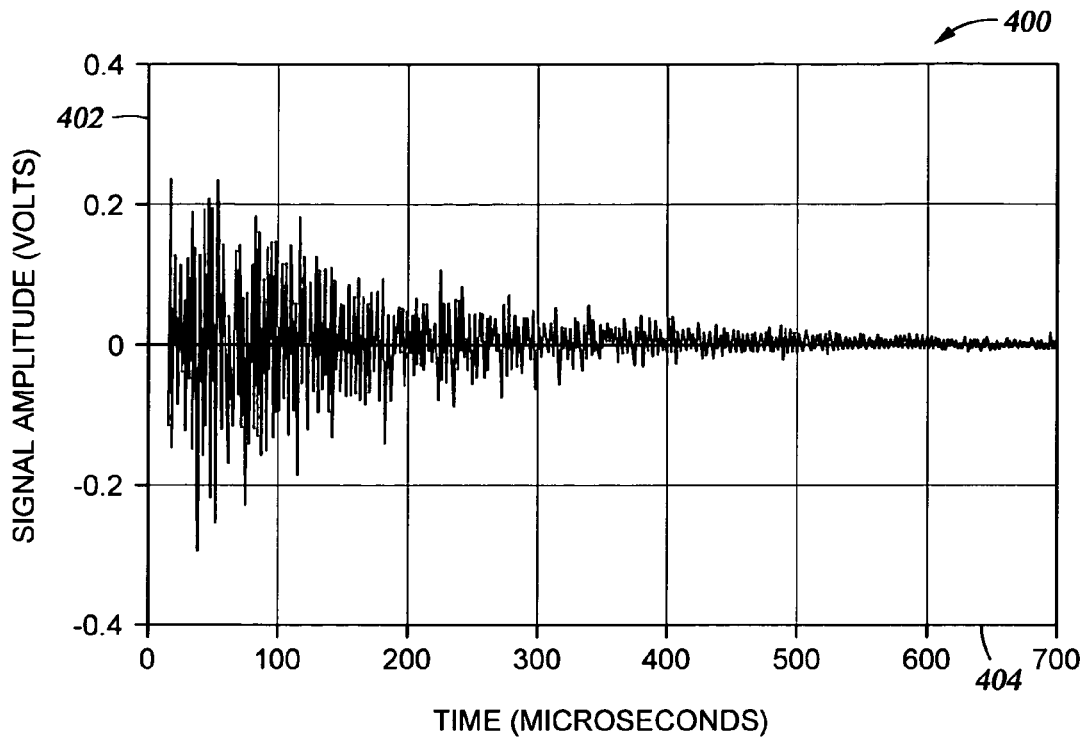
FIG. 4A shows the calibration response, C(t), which corresponds to the signal applied in FIG. 3A. This is the waveform that is collected by the calibration sensing device.

During the calibration procedure, the calibration sensor/acoustic capture device 290 is coupled to the output of the sonic resonator assembly (including coupling cone) 240 through the sample of composite material to be tested 282A. The objective is to capture a wave form that is produced as a response to the input stimulus being sent from the sonic resonator assembly 249. The capture waveform is shown in FIG. 4A after the wave travels through the composite material to a location at the sensor 290. This captured response to stimulus of the sonic resonator assembly by the capture device is then passed through the A/D converter and then to the computer for processing using the algorithm described in the following description of the calibration procedure.

Figure 3A:
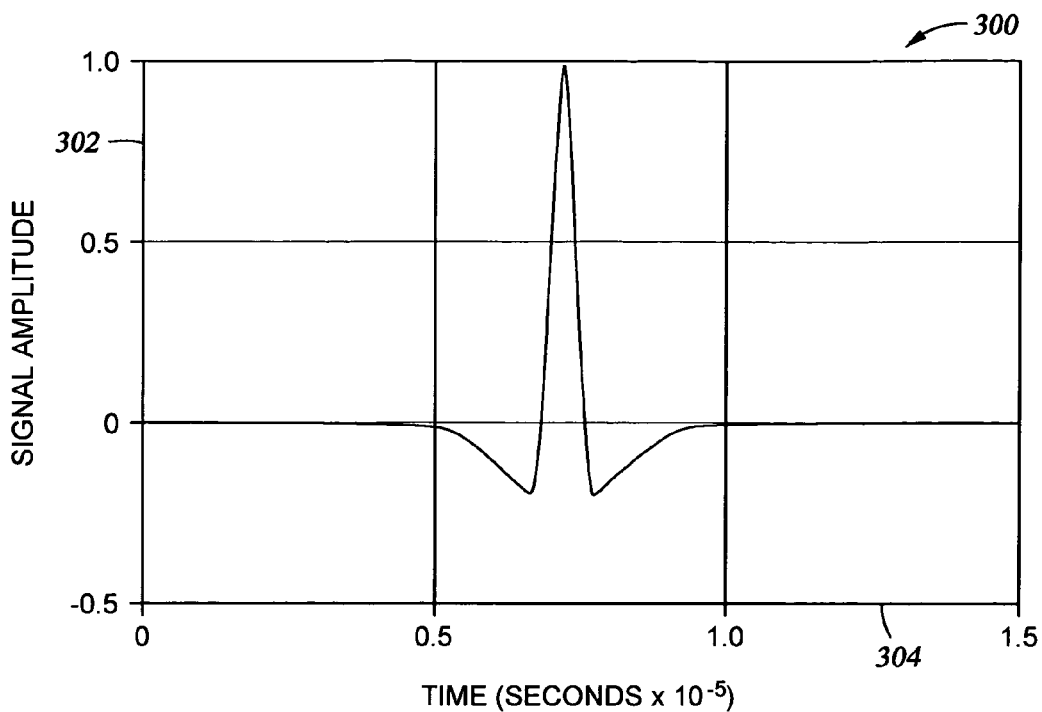
FIG. 3A is a plot 300 showing signal amplitude in volts on axis 302 as a function of time in seconds on axis 304 for an applied signal, I(t), used during the calibration method of the invention. This signal is a waveform applied to the resonator as a stimulus during calibration. The signal shape and polarity of this waveform is selected in accordance with the calibration Step 1 described in the Detailed Description, below. The positive waveform shown in FIG. 3A will create a compression wave in the material with application of the power packet. Inverting the waveform shown (to create a negative signal amplitude exiting from the computer/controller 110 illustrated in FIG. 1A) will create a rarefaction wave with the application of the power packet.
Figure 3B:
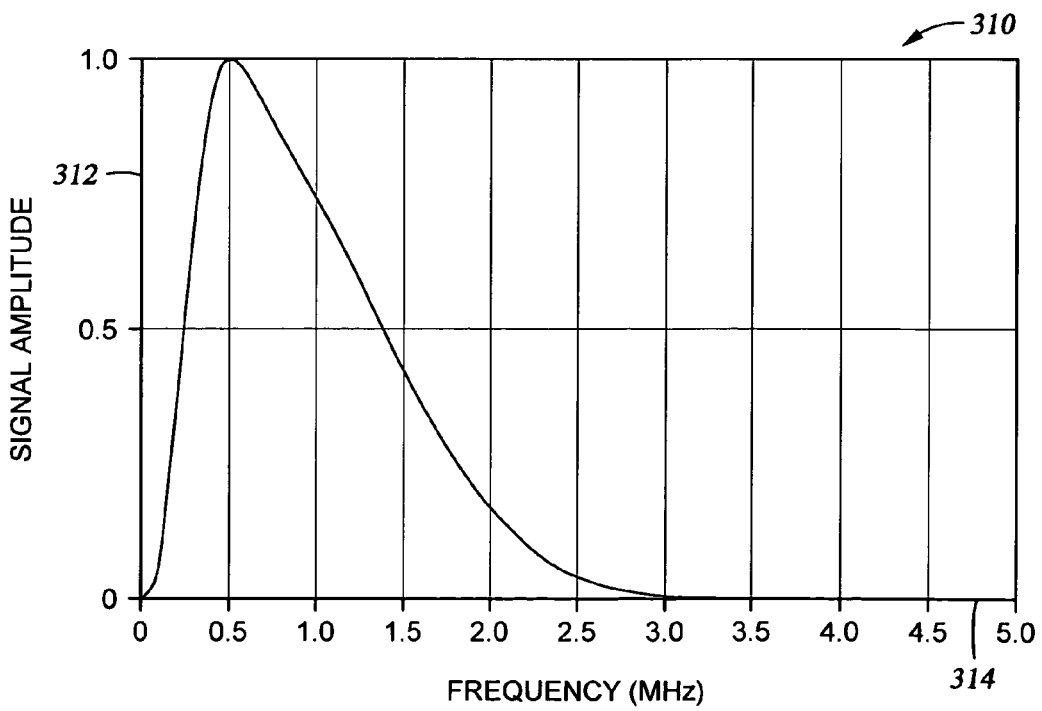
FIG. 3B shows the Fourier transform signal amplitude, $A_f$, on axis 312 as a function of the signal frequency in Hz ($\times 10^6$) on axis 314 for the applied voltage signal I(t) illustrated in FIG. 3A.

Calibration is performed using the following procedure:

1. Creating a broadband signal, I(t), to excite or stimulate the sonic resonator assembly. For convenience, a desired final response impulse will be used for calibration; however, any signal having the bandwidth of the desired impulse may be used, which could be a positive-followed-by-negative impulse, or any phase. FIGS. 3A and 3B, respectively, show the applied signal I(t) and amplitude $A_f$ transform for the applied signal. FIG. 3A is a plot 300 showing signal amplitude (in volts) on axis 302 as a function of time in seconds $\times 10^{-5}$ on axis 304. FIG. 3B is a plot 310 showing signal amplitude on axis 312 as a function of signal frequency in Hz ($\times 10^6$) on axis 314. For material testing, the optimal impulse would be as shown in FIG. 3A. A Fourier transform of this impulse or other signal provides an amplitude $A_f(f)$.

Figure 4B:
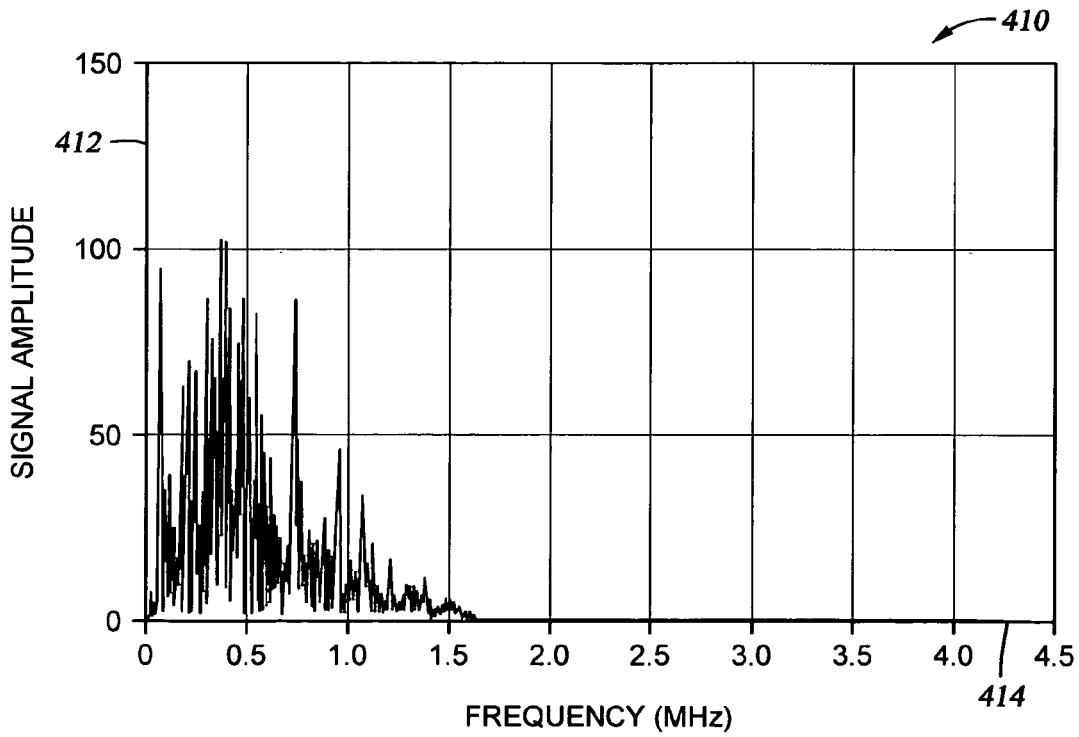
FIG. 4B shows the amplitude and spectral response, $A_C(f)$, which corresponds to the calibration response shown in FIG. 4A.

2. Applying the signal (as determined in Calibration Step 1, above) to the system and measuring the calibration response C(t), as shown in FIG. 4A, which is a plot 400 of signal amplitude (in volts) on axis 402, as a function of time in microseconds on axis 404. This is the signal captured at the calibration sensor device. Then taking the Fourier transform of this captured signal to obtain the amplitude and spectral response $A_C(f)$, as shown in FIG. 4B, which is a plot 410 of signal amplitude 412 as a function of signal frequency in MHZ (megahertz) on axis 414.

Figure 5A:
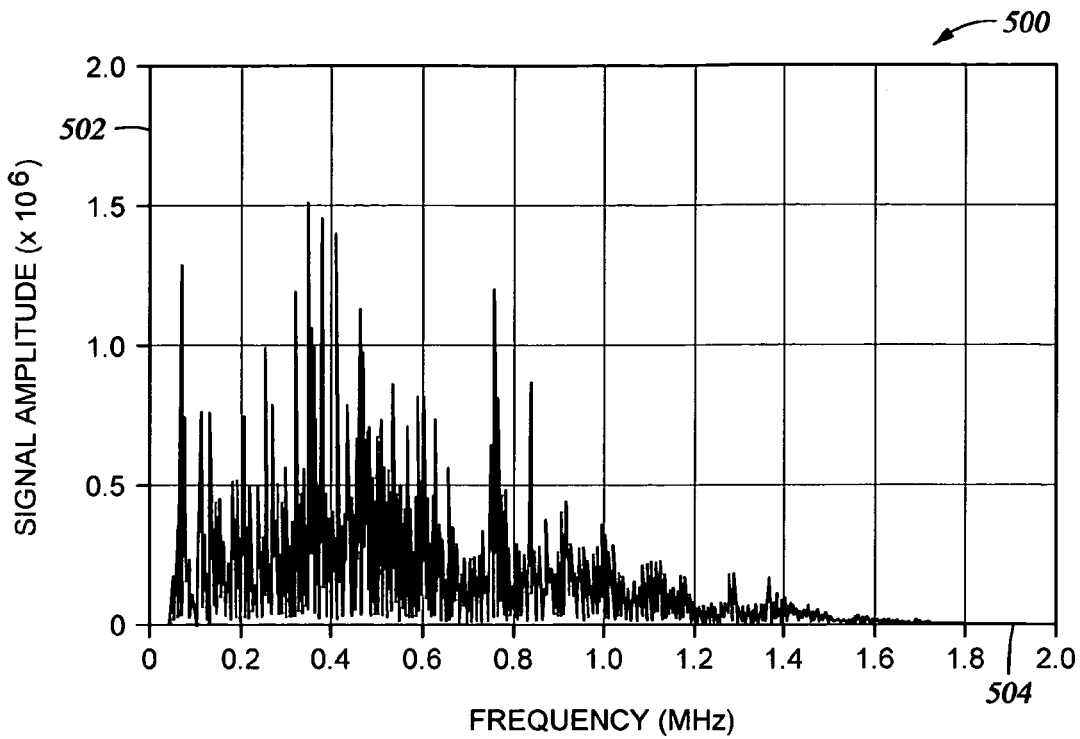
FIG. 5A shows the spectra of the calibration response, Ac(f) which is shown in FIG. 4B, but expanded for frequency resolution.
Figure 5B:
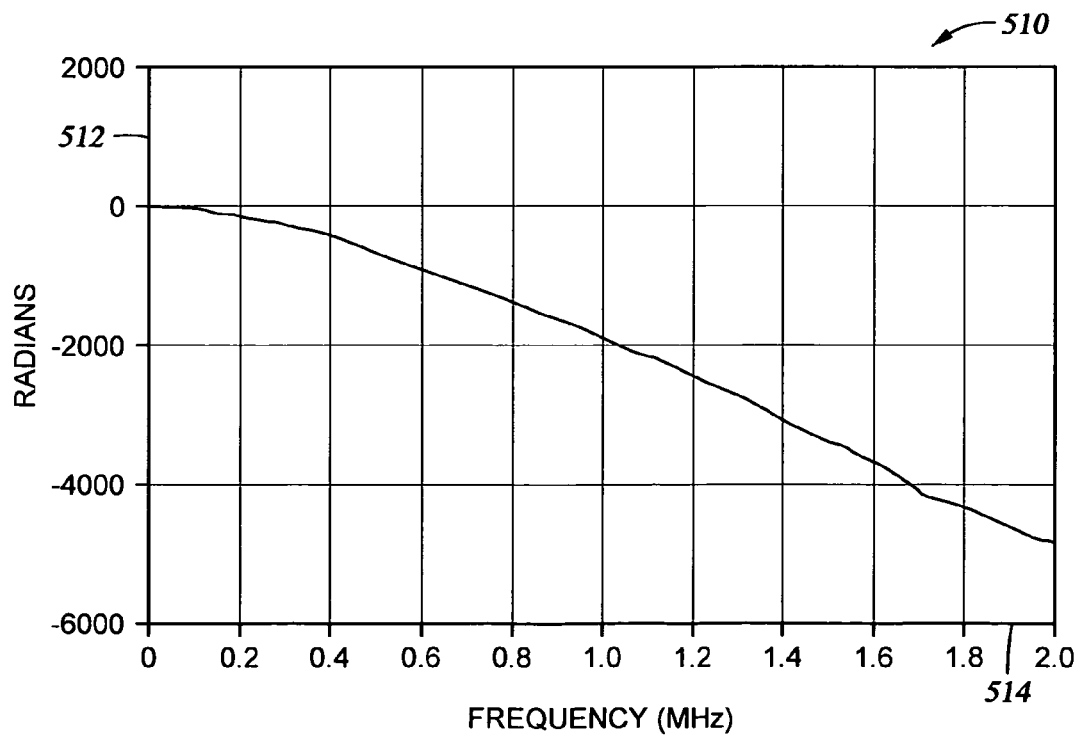
FIG. 5B shows the phase of the calibration response which correlates with the spectra shown in FIG. 5A.

3. Calculating the system phase shift $\delta$ (f)=$\theta_I(f)-\theta_C(s)$. FIGS. 5A and 5B, respectively, show the spectra and phase of the calibration response. FIG. 5A is a plot 500 showing signal amplitude on axis 502 as a function of signal frequency in MHZ on axis 504. FIG. 5B is a plot 510 of radians on axis 512 as a function of signal frequency in MHZ on axis 514.

Figure 6:
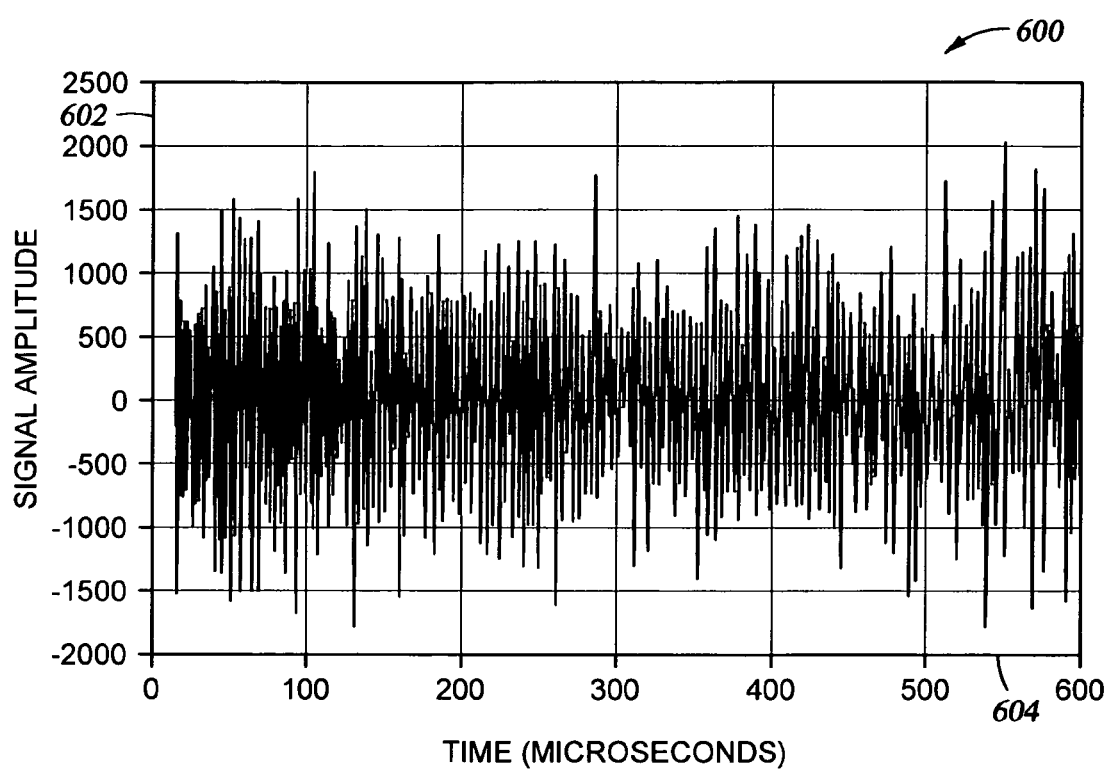
FIG. 6 shows the waveform (power packet) which results from the calibration procedure.

4. Taking the inverse Fourier transform of the amplitude function $A_s(f)$, and reversing the signal in time, to define the drive function that produces the desired signal. FIG. 6 shows the applied voltage signal used to create a pulse (based on Calibration Steps 1 through 3). FIG. 6 is a plot 600 showing signal amplitude on axis 602 as a function of time in microseconds on axis 604. The waveform ("power packet") shown in FIG. 6 is the result of the calibration procedure.

Referring back to FIGS. 2A and 2B, this wave form (power packet) is then passed through the D/A converter 220 and power amplifier 230 to the resonator assembly 240, which will produce a high-power, wide-bandwidth rarefaction pulse concentrated (focused) at the location where the calibration sensor 290 was previously located. During the bonded composite testing, composite panel 282A and calibration sensor 290 are replaced by bonded component 280, which includes front composite panel 282A, adhesive 284, and back composite panel 282B.

Figure 7A:
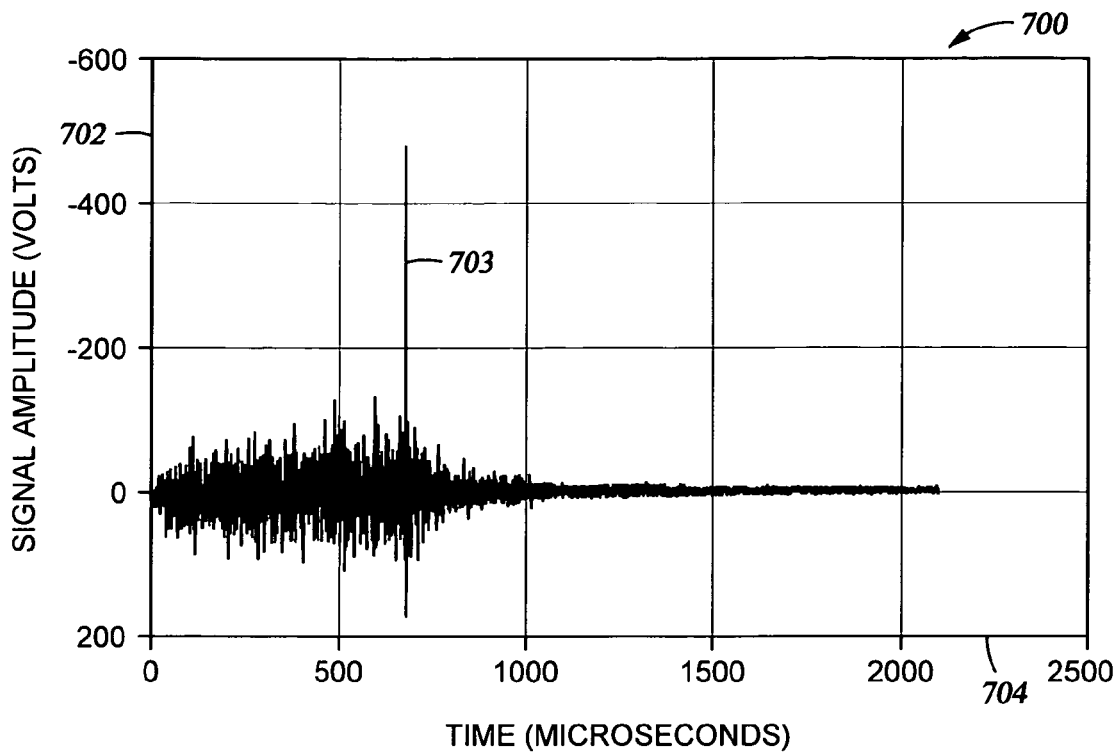
FIG. 7A shows a resultant power pulse 703 which is created when the waveform shown in FIG. 6 is processed through the sonic resonator system 100.
Figure 7B:
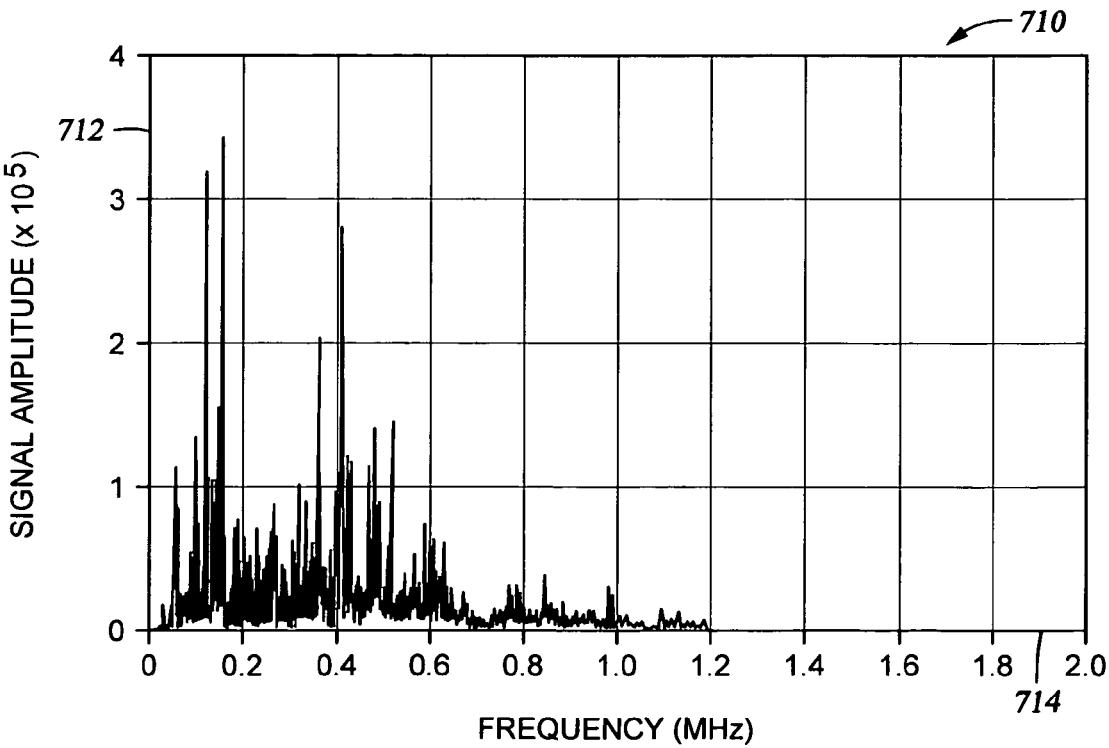
FIG. 7B shows the bandwidth of the power pulse 703 illustrated in FIG. 7A.

FIGS. 7A and 7B, respectively, show the resultant power pulse 703 produced and its bandwidth. FIG. 7A is a plot 700 showing signal amplitude (in volts) on axis 702 as a function of time in microseconds on axis 704. FIG. 7A shows the negative polarity of a rarefaction wave. The computer/controller 110 can be instructed to generate a wave having the desired polarity. FIG. 7B is a plot 710 showing signal amplitude 712 as a function of frequency in megahertz on axis 714, illustrating the bandwidth of the signal.

Before a discussion of the choice of the amplitude function, three measures of performance must be considered:

1. Peak Power: One measure of performance is the ratio of peak acoustic output power to average input electrical power. The practical question that must be asked is: What is the peak acoustic output power that can be obtained when using a drive amplifier-transducer combination that can deliver a maximum electrical output drive power?

2. Figure-of-Merit: Another measure of performance is the ratio of the peak acoustic output power to average acoustic output power. Configurations that produce high peak acoustic power at the specified time often have high leakage, that is, relative high acoustic output at other times.

3. Bandwidth: The bandwidth of the acoustic impulse determines the width of the impulse. Monocycle impulses require large bandwidths. Transducers designed according to the present invention can have bandwidths which exceed one decade and can produce short impulses. There may be applications that require that the bandwidth be limited, e.g., to avoid the beam spread that might occur at low frequencies. In this case, the transducer can be driven with a signal having a lower bandwidth.

The following are four methods of choosing the amplitude function, and the relative advantage and disadvantage of each method.

1. Choose the amplitude transform of the calibration response function (refer to FIG. 4B). This function produces a high-amplitude pulse with corresponding lower resonator losses (a lower figure-of-merit). This function has peaks of the amplitude transform at frequencies where there is good electrical impedance matching between the power amplifier and transducer and correspondingly efficient acoustic power generation by the transducer.

2. Choose the amplitude transform of the impulse used for calibration (refer to FIG. 3B). This function produces a higher figure-of-merit than the function described above, but a lower peak power, because energy is supplied to the transducer at frequencies where there is a poor electrical impedance match between the amplifier and transducer.

3. Choose $1/(A_c(f)+\epsilon)$, where $\epsilon$ is a small number to prevent this function from becoming infinite. This produces the highest figure-of-merit with the lowest peak power. In this case, high electrical amplitudes are applied to equalize the output spectrum at frequencies where the transducer has low electrical-to-acoustic efficiency.

4. Choose any of the above amplitude functions, but put the function through a window (such as a Hamming window) to limit the electrical bandwidth (hence, the acoustic bandwidth). The effect of this is to remove any unwanted acoustic frequencies from the output at the expense of making the impulse longer (i.e., the impulse will have many cycles).

Our experience has been that using a combination of methods 1 and 4 listed directly above provides the best results in determining whether a "kissing bond" is present.

5. Method of Using the Sonic Resonator System for Testing the Adhesive Bond Strength of Composite Materials Sonic testing using the sonic resonator system of the present invention is greatly simplified over conventional means of testing the adhesive bond strength of composite materials. Further, the sonic testing method of the invention can be conducted using a single attachment of the resonator assembly to a sample of the composite material to determine if the adhesive bond is of minimum strength.

A general test sequence using the sonic resonator system of the invention is as follows:

1. Attach the sonic resonator assembly to the bonded composite structure to be tested.

2. Run the depth calibration sequence where the computer will match the thickness of the panel from the pulse echo flight time to the adhesive bond with the proper signal sequence from a previous calibration using a look up table.

3. Run the adhesive test sequence.

4. Run (NDT) pulse echo sequence to obtain a pass/fail indication of delamination.

5. Detach the sonic resonator assembly from the test sample and attach it to the next bond location to be tested.

Calibration conducted as described in Section 3, above, using representative composite samples (composition and thickness) in the laboratory and saved in the computer as look-up tables for later field selection by the software algorithm and results from the pulse echo step, step 2.

The field testing (assuming the calibration was previously completed) of composite structures that are bonded together can be conducted using the following procedure: Referring back to FIG. 2B, the coupling cone 248 of the sonic resonator assembly 240 is attached to the outer, front surface 276 of the composite material sample 280 using an adhesive such as a cyanoacrylate (CA) adhesive. A cyanoacrylate works well because of its high tensile strength (>2000 lbs./sq. in.), and ability to remain in contact with the surface of the test sample. The sonic intensity between the tip of coupling cone 248 and the composite material sample 280 is an average sonic field of moderate intensity and not the high intensity rarefaction wave focused at location of bonding within the composite material. When testing is completed, the sonic resonator assembly 240 can be easily detached from the composite material sample 280 by creating a shear stress, for example, by striking the side of the resonator assembly to break the cyanoacrylate adhesive bond. The shear strength of cyanoacrylate adhesive is typically a fraction of its tensile strength.

After the sonic resonator coupling cone 248 is attached to the outer, front surface 276 of sample 280, the sonic resonator assembly is operated in the pulse echo mode using the piezoelectric driver 242 to send a wide-bandwidth, low-intensity pulse into the composite structure and capture the return echo, using a receive element (typically a transparent receiver assembly 150) to determine the depth of the adhesive bond. After the depth is determined using the pulse echo mode, a look-up table (from previous laboratory sample calibration) is used to select where the reconstructed "focus" of maximum rarefaction will occur.

The sonic resonator assembly 249 is then operated in its high-power mode to generate a series of rarefaction power pulses into the sample of material 280 under test. After running the power pulse sequence, the sonic resonator assembly 249 may be again run in pulse echo mode to determine if the adhesive bond had delaminated. If a void (i.e., delamination) is present, the echo amplitude of the return signal from the depth where the bond is located will be of much higher intensity, indicating a weak bond that has delaminated.

In one embodiment of the invention, the discs which make up the resonator assembly 249 may be altered in a manner which increases the efficiency of the transfer of the plane wave through the assembly 249, providing an increased magnitude of the plane wave.

FIG. 8A shows a surface view and FIG. 8B shows the matching cross-sectional view of a resonator disc 802 which has a radial kerf 808 cut into a surface 803 of disc 802. The purpose of the radial kerf is to align in time the radial surface wave with the plane wave reverberation in a given disk, to improve the efficiency of the resonator assembly. A number of kerfs may be used on a disc surface, depending on the diameter of the disc.

Figure 8C:
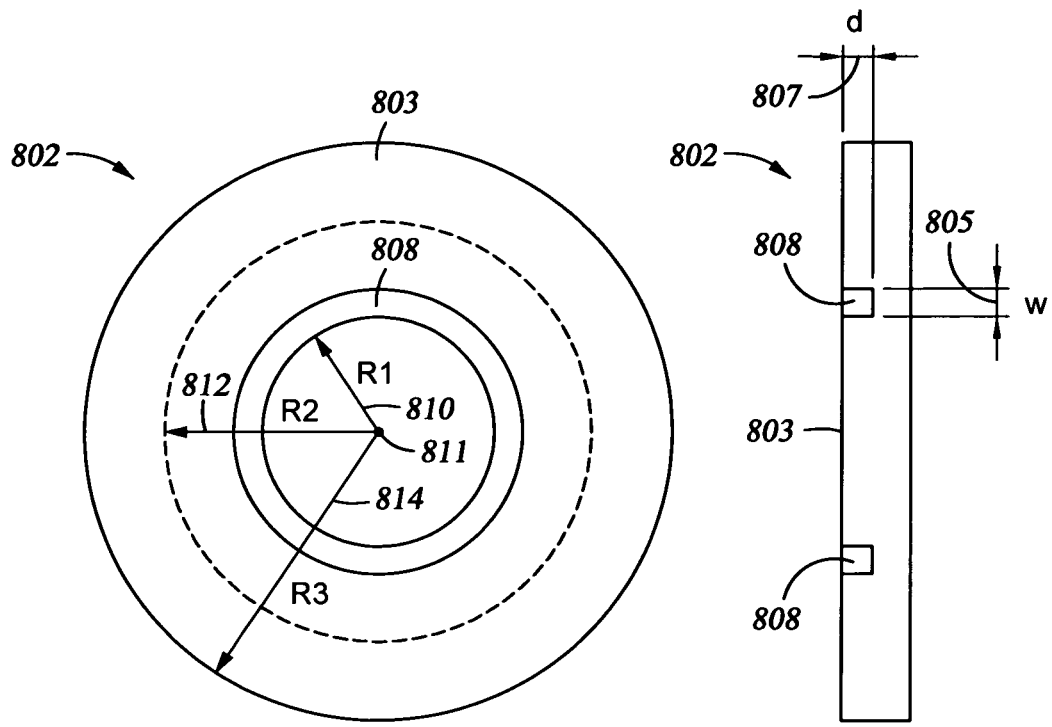
FIG. 8C shows the propagation and direction 822 of a plane wave, with reference numeral 824 indicating the resulting radial surface wave generated by the passing of plane wave 822 at the interface 833, and reference numeral 828 indicating the resulting radial surface wave generated by the passing of plane wave 822 at the interface 835. Cutting of a kerf of the kind shown in FIG. 8A into the front face of the disc (facing the incoming wave) aligns (in time) the radial surface wave with the plane wave reverberation in that disc, so both waves reach an acoustic peak at the same time. Typically, kerfs are cut in selected discs, but may alternatively be cut into each disc. As the amplitude of the plane wave diminishes after passing through the resonator stack, there is less advantage in having the kerfs present.
Figure 8C:
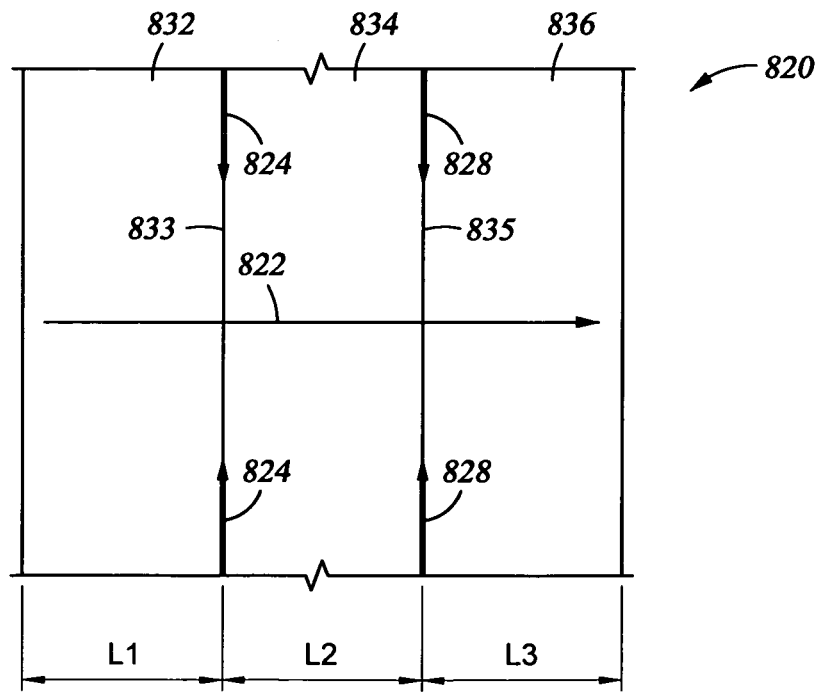

Since the main resonator assembly comprises lamina of metallic discs, when the plane (longitudinal) wave generated by the piezoelectric element strikes the discontinuity between any two of these discs having different acoustic characteristics, various additional waves are generated. The major sound wave generated as a result of the primary plane wave striking the interface between two discs is a radial surface wave which is sometimes referred to as a plate wave. This radial surface wave starts from the impedance discontinuity at the outer radius of each metallic disc when the generated plane wave passes the interface between lamina (discs). With reference to FIG. 8C, which shows a cross-sectional view 820 of disc lamina L1, L2, and L3, the radial surface wave velocity created at laminal interfaces 832 and 833 is dependent in a very complicated way on the material, its thickness, the material to which it is joined and the ultrasonic frequency. This velocity is more easily obtained by laboratory measurement rather than trying to calculate it. The measured velocity of this radial surface wave is in the range of 2000 msec and is about one third of the plane wave velocity in a typical disc. FIG. 8C shows the generation of radial surface waves 824 and 828 which occur at the interfacial surfaces 833 and 835 between the disc laminae L1, L2, and L3. With reference to the disc 802 top view illustrated in FIG. 8A, the radial surface wave will reach a peak at the center 811 of the disk 802, and will repeat each odd multiple of the Flight Time from the disc edge to the center, where Radial Flight Time(t) is calculated as follows:

$$RFT(t) = \text{Radial Distance}(Rd)/\text{Velocity}(V) \text{ of the surface wave}$$

This RFT(t) is then the time for the radial surface wave to travel from the outer circumference of the disc to the center and then repeats when traveling through the center to the outer edge and then back to the center again, resulting in the odd multiple of Flight Time, i.e., 1, 3, 5, etc.

In one embodiment of the invention, the RFT is matched to the 2 way PFT of the plane wave 822, illustrated in FIG. 3C for a given disc. Where the PFT of the plane wave in the given disc is:

$$PFT(t) = \text{Disk Thickness}(X_d)/\text{Velocity}(V) \text{ of the plane wave}$$

Because the radius of the disk in a resonator assembly may not allow for the desired alignment (in time) of the radial surface wave with the plane wave in a given disc, a radial kerf is cut into the disc to establish the proper FT alignment of the radial surface wave with the FT of the plane wave. The kerf creates a new "edge" for the radial surface wave to form and start from.

The radius at which the kerf is cut into the disc is determined by:

$$R_{kerf} = 2 * FT_{plane\,wave} * V_{radial\,wave}/N$$

where N is odd integer values 1, 3, 5, etc.

The result of cutting a kerf in a metallic disk equal to $R_{kerf}$ is to align (in time) the radial surface wave with the plane wave reverberation in that disk, so that both waves reach an acoustic peak at the same time. Addition of a kerf improves the efficiency of the resonator by "capturing" the acoustic radial surface wave energy that would normally be a lossy or destructive wave it were not forced to properly align with the plane wave. Typically, kerfs are cut in selected discs, but may alternatively be cut into each disc. As the amplitude of the plane wave diminishes after passing through the resonator stack, there is less advantage to having kerfs.

FIG. 8B shows a cross-sectional view of FIG. 8A, illustrating the radial kerf 808 and the depth and width of the kerf. Cutting of a kerf of the kind shown in FIG. 8A into the front face of the disc aligns (in time) the radial surface wave with the plane wave reverberation in that disc, so both waves reach an acoustic peak at the same time.

FIG. 8A shows the position of a kerf 808 in a typical disc 802 which may be present in a main resonator assembly 144 of the kind shown in FIGS. 1A and 1B. The radius "R1" (810) shown in FIG. 8A is the $R_{kerf}$ that was calculated from the equation provided above. The width of the kerf, illustrated as "w" (805) on cross-sectional view of disc 802, which is provided in FIG. 8B, should be less than 0.030 inch and have a minimum depth of 0.030 inch with a maximum depth of half of the thickness of the disc.

"R2" (812) illustrated in FIG. 8A shows the location of a second radial surface wave peak that results from cutting a kerf at R1. This new radial wave peak occurs at half the difference in distance between the kerf at R1 and the outer radius "R3" (814) illustrated in FIG. 8A. Given the largest disc radius and the taper of a typical main resonator assembly, the acoustic peak of the second radial surface wave at R2 may also not align with the acoustic peak of plane wave per the $R_{kerf}$ equation, so that so both waves reach an acoustic peak at the same time.

The addition of a second kerf (not shown) with the proper radius (as calculated using the $R_{kerf}$ equation) would align the plane and radial surface waves. A third kerf could be cut to again align this new radial surface in time with the plane wave. A practical limit will quickly be reached for additional kerfs beyond two kerfs in a single disc, unless the discs are greater than 2 inches in diameter.

We have seen at least 20% improvement with a single kerf cut in the first two discs in the assembly. The effect was in the amplitude of the delivered power pulse.

The above described exemplary embodiments are not intended to limit the scope of the present invention, as one skilled in the art can, in view of the present disclosure, expand such embodiments to correspond with the subject matter of the invention claimed below.

We claim:

1. A sonic resonator system which is used to apply a power pulse in the form of a rarefaction wave at a selected location within a composite structure, wherein said system comprises:
   a computer containing software algorithms for signal reconstruction and a wave form generator;
   a digital-to-analog converter which is in communication with said wave form generator;
   a power amplifier;
   a sonic resonator assembly which transmits sonic energy into said composite structure, where said sonic energy includes a power pulse of a wide-bandwidth rarefaction wave generated using input from said wave form generator; and a removable calibration sensor which enables said resonator system to be calibrated to work in combination with a particular composite material, and wherein said calibration sensor is located in series after said sonic resonator assembly and after a location at which a sample of composite material is placed between said sonic resonator assembly and said calibration sensor, for purposes of calibration of said sonic resonator system.

2. A sonic resonator system in accordance with claim 1, wherein said sonic resonator assembly also comprises a transparent receiver assembly which is used in echo mode for determination of an effect of application of said power pulse within said composite structure.

3. A sonic resonator system in accordance with claim 2 or claim 1, wherein said composite structure is a bonded composite structure, and wherein said power pulse is designed to be applied in time so that said power pulse occurs at a location present between a first layer or panel of composite material and a second layer or panel of composite material, where a bonding material is present between said first layer or panel and said second layer or panel.

4. A sonic resonator assembly in accordance with claim 2, wherein said transparent receiver assembly is a three disc structure having a center disc of piezoelectric element sandwiched between two metal-comprising exterior discs, where said exterior discs are selected to match the impedance of the piezoelectric element.

5. A sonic resonator system in accordance with claim 1, wherein said system also includes a pre-amplifier which follows said calibration sensor and an analog to digital convertor which follows said pre-amplifier and which is in communication with said computer.

6. A sonic resonator system in accordance with claim 1 or claim 5, wherein said calibration sensor is an acoustic capture device.

7. A sonic resonator system in accordance with claim 1, wherein a transducer present within said sonic resonator system has a bandwidth which exceeds one decade, so that short power pulses can be produced.

8. A sonic resonator system in accordance with claim 1, wherein said computer algorithms enable putting an amplitude function through a window to limit acoustic bandwidth of said power pulse.

9. A sonic resonator system in accordance with claim 1, wherein said sonic resonator assembly includes discs where a surface of at least one disk has been altered by forming at least one kerf in said disc, so that the efficiency of the resonator assembly is improved.

10. A sonic resonator system in accordance with claim 9, wherein said kerf is a radial kerf.

11. A sonic resonator assembly in accordance with claim 9, wherein at least a portion of said discs present in a main resonator assembly are of a construction which alternates between a high Z acoustic material and a low Z acoustic material.

12. A sonic resonator assembly in accordance with claim 11, wherein an impedance ratio between a disc containing a wave before an interface and a disc containing a wave after an interface ranges from about 1.3:1 and about 3:1.

13. A sonic resonator assembly in accordance with claim 12, wherein a high Z acoustic material is selected from the group consisting of nickel, platinum, gold, molybdenum, and combinations thereof, and a low Z acoustic material is selected from the group consisting of aluminum, tin, titanium, indium, and combinations thereof.

* * * * *